United States Patent
Moses et al.

(10) Patent No.: US 9,770,601 B2
(45) Date of Patent: Sep. 26, 2017

(54) MAGNETIC CONFIGURATION AND TIMING SCHEME FOR TRANSCRANIAL MAGNETIC STIMULATION

(71) Applicant: YEDA RESEARCH AND DEVELOPMENT CO. LTD., Rehovot (IL)

(72) Inventors: Elisha Moses, Rehovot (IL); Assaf Rotem, Rehovot (IL)

(73) Assignee: YEDA RESEARCH AND DEVELOPMENT CO. LTD., Rehovot (IL)

(*) Notice: Subject to any disclaimer, the term of this patent is extended or adjusted under 35 U.S.C. 154(b) by 43 days.

(21) Appl. No.: 14/714,368

(22) Filed: May 18, 2015

(65) Prior Publication Data
US 2015/0246238 A1 Sep. 3, 2015

Related U.S. Application Data

(62) Division of application No. 13/254,361, filed as application No. PCT/IL2010/000171 on Mar. 2, 2010, now Pat. No. 9,067,052.

(Continued)

(51) Int. Cl.
*A61N 1/00* (2006.01)
*A61N 2/00* (2006.01)
(Continued)

(52) U.S. Cl.
CPC ............ *A61N 2/006* (2013.01); *A61B 5/0484* (2013.01); *A61B 5/4836* (2013.01);
(Continued)

(58) Field of Classification Search
CPC ............ A61N 2/02; A61N 2/004; A61N 2/12
See application file for complete search history.

(56) References Cited

U.S. PATENT DOCUMENTS 6,066,084 A 5/2000 Edrich et al.
6,149,576 A 11/2000 Gray et al.
(Continued)

FOREIGN PATENT DOCUMENTS

EP 0913167 A2 5/1999
JP 2000-254239 9/2000
(Continued)

OTHER PUBLICATIONS

Brasil-Neto, J. P. et al. Optimal focal transcranial magnetic activation of the human motor cortex: effects of coil orientation, shape of the induced current pulse, and stimulus intensity. J Clin Neurophysiol 9, 132-6 (1992).

(Continued)

*Primary Examiner* — Amanda Patton
*Assistant Examiner* — Philip C Edwards
(74) *Attorney, Agent, or Firm* — Mark S. Cohen; Pearl Cohen Zedek Latzer Baratz LLP

(57) ABSTRACT

Transcranial magnetic stimulation (TMS) is a remarkable tool for probing the brain. However, it is still unclear why specific regions in the cortex are excitable by TMS while others are not. This invention provides methods and tools for the design of efficient magnetic stimulators. Such stimulators can excite neuronal networks that were not sensitive to stimulation until now. Stimulation can be carried out both in-vitro and in-vivo. Novel systems and techniques of this invention will enable both treatment and diagnostics by stimulating regions of the brain or neuronal assemblies that were previously unaffected by TMS.

11 Claims, 10 Drawing Sheets

Related U.S. Application Data

(60) Provisional application No. 61/156,835, filed on Mar. 2, 2009.

(51) Int. Cl.

| | | |
|---|---|---|
| *A61N 1/36* | (2006.01) | |
| *A61N 2/02* | (2006.01) | |
| *A61B 5/0484* | (2006.01) | |
| *A61B 5/00* | (2006.01) | |
| *A61N 1/08* | (2006.01) | |
| *A61N 1/40* | (2006.01) | |

(52) U.S. Cl.
CPC .......... *A61N 1/36025* (2013.01); *A61N 2/02* (2013.01); *A61N 1/08* (2013.01); *A61N 1/36082* (2013.01); *A61N 1/40* (2013.01)

(56) References Cited

U.S. PATENT DOCUMENTS

| | | | |
|---|---|---|---|
| 6,179,771 | B1 | 1/2001 | Mueller |
| 7,471,974 | B2 | 12/2008 | Hartlep et al. |
| 2002/0097125 | A1 | 7/2002 | Davey |
| 2002/0099256 | A1* | 7/2002 | Manne ............... A61N 1/40 600/9 |
| 2004/0078056 | A1 | 4/2004 | Zangen et al. |
| 2005/0113630 | A1* | 5/2005 | Fox ............... A61N 2/02 600/13 |
| 2005/0182288 | A1* | 8/2005 | Zabara ............ A61N 1/36025 600/14 |
| 2006/0199992 | A1 | 9/2006 | Eisenberg |
| 2006/0264691 | A1 | 11/2006 | Rohan |
| 2007/0260107 | A1 | 11/2007 | Mishelevich |

FOREIGN PATENT DOCUMENTS

| | | |
|---|---|---|
| WO | WO 99/55421 A1 | 11/1999 |
| WO | WO 00/78267 | 12/2000 |
| WO | WO 2006/134598 | 12/2006 |
| WO | WO 2007/130308 | 11/2007 |
| WO | WO 2007/145838 A2 | 12/2007 |
| WO | WO 2008/066509 A2 | 6/2008 |

OTHER PUBLICATIONS

Breskin, I., Soriano, J., Moses, E. & Tlusty, T. Percolation in living neural networks. Phys Rev Lett 97, 188102 (2006).

Dubach, P., Guggisberg, A. G., Roster, K. M., Hess, C. W. & Mathis, J. Significance of coil orientation for motor evoked potentials from nasalis muscle elicited by transcranial magnetic stimulation. Clin Neurophysiol 115, 862-70 (2004).

Feinerman, O., Rotem, A. & Moses, E. Reliable neuronal logic devices from patterned hippocampal cultures. Nature Physics 4, 967-73 (2008).

Hallett, M. Transcranial magnetic stimulation: a primer. Neuron 55, 187-99 (2007).

Huang, Y. Z., Edwards, M. J., Rounis, E., Bhatia, K. P. & Rothwell, J. C. Theta burst stimulation of the human motor cortex. Neuron 45, 201-6 (2005).

Kammer, T., Beck, S., Thielscher, A., Laubis-Herrmann, U. & Topka, H. Motor thresholds in humans: a transcranial magnetic stimulation study comparing different pulse waveforms, current directions and stimulator types. Clin Neurophysiol 112, 250-8 (2001).

Kosel, M., Frick, C., Lisanby, S. H., Fisch, H. U. & Schlaepfer, T. E. Magnetic seizure therapy improves mood in refractory major depression. Neuropsychopharmacology 28, 2045-8 (2003).

Lisanby, S. H., Luber, B., Schlaepfer, T. E. & Sackeim, H. A. Safety and feasibility of magnetic seizure therapy (MST) in major depression: randomized within-subject comparison with electroconvulsive therapy. Neuropsychopharmacology 28, 1852-65 (2003).

Lisanby, S. H., Schlaepfer, T. E., Fisch, H. U. & Sackeim, H. A. Magnetic seizure therapy of major depression. Arch Gen Psychiatry 58, 303-5 (2001).

Mills, K. R., Boniface, S. J. & Schubert, M. Magnetic brain stimulation with a double coil: the importance of coil orientation. Electroencephalogr Clin Neurophysiol 85, 17-21 (1992).

Office Action for Japanese Patent Application No. 2011-552573 Dated Dec. 17, 2013.

Papa, M., Bundman, M. C., Greenberger, V. & Segal, M. Morphological analysis of dendritic spine development in primary cultures of hippocampal neurons. J Neurosci 15, 1-11 (1995).

Pascual-Leone, A., Cohen, L. G., Brasil-Neto, J. P. & Hallett, M. Non-invasive differentiation of motor cortical representation of hand muscles by mapping of optimal current directions. Electroencephalogr Clin Neurophysiol 93, 42-8 (1994).

Rotem, A. & Moses, E. Magnetic stimulation of one-dimensional neuronal cultures. Biophys J 94, 5065-78 (2008).

Roth, B.J. & Basser, P.J. A model of the stimulation of a nerve fiber by electromagnetic induction. IEEE Trans Biomed Eng 37, 588-597 (1990).

Soriano, J., Rodriguez-Martinez, M., Tlusty, T. & Moses, E. Development of Input Connections in Neural Cultures. Proc Natl Acad Sci U S A in press (2008).

Tings, T., Lang, N., Tergau, F., Paulus, W. & Sommer, M. Orientation-specific fast rTMS maximizes corticospinal inhibition and facilitation. Exp Brain Res 164, 323-33 (2005).

Zandieh, S., Hopf, R., Redl, H. & Schlag, M. G. The effect of ketamine/xylazine anesthesia on sensory and motor evoked potentials in the rat. Spinal Cord 41, 16-22 (2003).

Zangen, A., Roth, Y., Voller, B. & Hallett, M. Transcranial magnetic stimulation of deep brain regions: evidence for efficacy of the H-coil. Clin Neurophysiol 116, 775-9 (2005).

* cited by examiner

| S.N. | culture age (DIV) | Induced field Threshold (V/m) | | |
|---|---|---|---|---|
| | | Single horizontal coil | Single vertical coil | Crossed coil (Rotating field) |
| 1 | 21 | horizontal coil was not used in these experiments | | |
| 2 | 18 | | | |
| 3 | 29 | | | |
| 4 | 18 | | | |
| 5 | 15 | | | |
| 6 | 26 | | | |
| 7 | 26 | | | |
| 8 | 11 | | | |
| 9 | 11 | | | |
| 10 | 29 | | | 440 |
| 11 | 15 | | | 440 |
| 12 | 8 | | 510 | 440 |
| 13 | 8 | | | 400 |
| 14 | 23 | 350 | | 360 |
| 15 | 20 | 460 | Vertical coil not used in these experiments | |
| 16 | 25 | 770 | | |
| 17 | 16 | | | |
| 18 | 16 | | | |
| 19 | 15 | | | |
| 20 | 22 | | | |
| 21 | 15 | | | |
| 22 | 17 | | | |
| 23 | 16 | | | |
| 24 | 14 | | | |
| 25 | NA | | | |
| 26 | NA | | | |
| 27 | NA | | | |

Figure 4

|  | 2D culture | | Rat | |
| --- | --- | --- | --- | --- |
|  | Responded to stimulation | Electric Threshold | Responded to stimulation | Electric Threshold |
| Cross coil | 50% | 360±40 V/m | 89% | 250±10 V/m |
| Single coil | 13% | 380±30 V/m | 44% | 280±10 V/m |

MAGNETIC CONFIGURATION AND TIMING SCHEME FOR TRANSCRANIAL MAGNETIC STIMULATION

CROSS-REFERENCE TO RELATED APPLICATIONS

This application is a Divisional application from U.S. application Ser. No. 13/254,361, filed Sep. 1, 2011; which is a National Phase Application of PCT International Application No. PCT/IL2010/000171, International Filing Date Mar. 2, 2010; which claims the benefit of U.S. Provisional Patent Application No. 61/156,835 filed Mar. 2, 2009 which are incorporated in their entirety herein by reference.

FIELD OF THE INVENTION

This invention is related to transcranial magnetic stimulation (TMS), devices, apparatus and methods of use thereof.

BACKGROUND OF THE INVENTION

Transcranial magnetic Stimulation (TMS) is the leading noninvasive device for the stimulation of brain and nerve activity. As such, a significant increase in the variety of applications for TMS, from therapeutic treatments for depression or migraine to probing brain activity in a large number of research topics is seen. TMS is a novel and innovative addition to the arsenal of noninvasive probing capabilities and intervention modalities. The development of such probes is one of the major issues of diagnostic and therapeutic approaches to neurology and neurosurgery. The major limitation of TMS is the precision and specificity of its activation region. TMS is currently able to excite only specific areas in the brain, mostly in the cortex. It is still not obvious what determines the accessibility of brain areas to magnetic stimulation.

Transcranial Magnetic Stimulation (TMS) is a noninvasive technology for stimulating the brain that shows much promise for both research and clinical use. However, the basic technology has basically remained unchanged, and advances in its application have been far and few. Recent developments have concentrated both on the ability to deliver pulses at a high frequency repetition rate and on reaching deeper regions of the brain. This has been motivated in part by the hope of replacing the effective yet highly intrusive Electro Convulsive Therapy (ECT) for depression that is not responsive to drugs. However, a main limitation of TMS at this stage of its development is the highly specific directionality of the applied field, which demands a precisely targeted application that is extremely sensitive to motion and disturbances. Both location and orientation must be determined with high resolution and once an optimal position is determined, the magnet must be kept there during all the treatment. Stable and reproducible positioning can be achieved using MRI imaging and stereotactic positioning, but a device that ameliorates the directional sensitivity and enables a more efficient mode of applying TMS is a goal for development of future magnets.

The directional sensitivity arises because neurons are excited only if their axons are directed precisely along the induced electric field.

It was recently demonstrated that neuronal cultures are a major enabling tool for the development of TMS, with which new magnets, drug and TMS combination treatments, new protocols and other innovations can be screened and tested with no need for animal or human subjects. The ability to create action potential responses in cultures relies on two properties, namely size and orientation.

The dependence on orientation arises because the magnetic stimulation of a neuron occurs at the axon, whose projection along the induced electric field is the relevant parameter for achieving excitation. Using quasi-one-dimensional patterned cultures, axons could be directed to grow along rings concentric with the magnet, thus forcing them to have an extensive projection along the induced electric field. It should be noted that if it was possible to excite neurons by initiating an action potential in the dendrites then the situation would change, and the directionality would not be as crucial. Embodiments of such excitation are described herein below.

Another important feature that has been identified is that the initial excitation is achieved by stimulating a subpopulation of especially sensitive neurons, which then serve as a nucleating center for the firing of the whole network. In a culture that has been completely disconnected by applying receptor antagonists (CNQX, APV and Bicuculline), only this small subset (about 1 percent) is active and responds to magnetic stimulation. When the culture is connected, this kernel is responsible for eliciting a population response of all neurons in the network. If the size of the kernel is too small, the driving input into neurons in the network is not enough for initiating the population response.

To achieve a population response to magnetic stimulation, one must therefore excite action potentials in a large number of initiating neurons. In a neuronal network whose axonal orientation is random, this requirement is difficult to meet using conventional TMS, since the orientation of its induced field is constant and the probability that a large enough number of axons will be directed along this field is low.

SUMMARY OF THE INVENTION

In one embodiment, this invention provides a method for improved neuron excitation, the method comprising subjecting one or more neurons to a rotating electric field, thereby exciting said neuron or said neurons. In one embodiment, the rotating electric field is the resultant sum of at least two time-dependent electric fields.

In one embodiment, the at least two time-dependent electric fields are induced by at least two time-dependent magnetic fields. In one embodiment, the at least two time-dependent magnetic fields are induced by passing currents through at least two separate and independent coils.

In one embodiment, the two separate and independent coils are driven with shifted phases in time of said currents. In one embodiment, the coils create at least two time-dependent electric fields, whose resultant sum changes orientation in time.

In one embodiment, the at least two time-dependent fields are at an angle with respect to each other. In one embodiment, the angle is a 90 degree angle.

In one embodiment, the two coils are independently driven. In one embodiment, the two coils are independently driven by two power supplies.

In one embodiment, the two coils are at an angle with respect to each other. In one embodiment, the two coils are at a right angle with respect to each other and are perpendicular to each other.

In one embodiment, the currents passed through the at least two coils comprise: a first current passed through a first coil and a second current passed through a second coil such that said first current has a phase with respect to said second current. In one embodiment, the phase of the first current with respect to the second current is a 90 degree phase.

In one embodiment, the first current is pulsed and the second current is pulsed.

In one embodiment, the number of the pulses of the first current and of the second current is one or is greater than one.

In one embodiment, the pulse of the first current comprises a first sine wave and the pulse of the second current comprises a second sine wave such that the second sine wave lags by one quarter of a cycle behind the first sine wave.

In one embodiment, the pulse of the first current comprises one period of the first sine wave and the pulse of the second current comprises one period of the second sine wave.

In one embodiment, the rotating electrical field is generated using an electrode assembly comprising at least two pairs of electrodes. In one embodiment, at least two voltages are applied to the at least two pairs of electrodes in the electrode assembly. In one embodiment, the voltages vary in time. In one embodiment, the at least two pairs of electrodes are at an angle with respect to each other. In one embodiment, the two pairs of electrodes are at a right angle with respect to each other and are perpendicular to each other.

In one embodiment, the neuron excitation comprises axonal excitation. In one embodiment, the method is applied to a brain of a subject. In one embodiment, the method is applied for diagnostics. In one embodiment, the method is applied for treatment.

In one embodiment, neuron excitation is applied to a neuron culture. In one embodiment, response of said culture to said neuron excitation is detected.

In one embodiment, the rotating field excites the axons of said neurons, wherein the direction of the long axis of one axon creates a non-zero angle with respect to the direction of the long axis of a second axon. In one embodiment, the rotating electric field excites at least the minimal number of neurons needed to generate a response in a neuron population, thereby generating a global response in said neuron population.

In one embodiment, the long axes of the axons of at least two of said neurons are not parallel.

In one embodiment, this invention provides a device for improved neuron excitation, said device comprising a set of at least two separate coils. In one embodiment, the at least two separate coils are driven with shifted phases of current in time. In one embodiment, the coils create at least two time-dependent electric fields, whose resultant sum changes orientation in time. In one embodiment, the two coils are independently driven. In one embodiment, the two coils are independently driven by two power supplies.

In one embodiment, the two coils are at an angle with respect to each other. In one embodiment, the two coils are at a right angle with respect to each other and are perpendicular to each other.

In one embodiment, the currents passed through the at least two coils comprise: a first current passed through a first coil and a second current passed through a second coil such that the first current has a phase with respect to the second current. In one embodiment, the phase of the first current with respect to the second current is a 90 degree phase.

In one embodiment, the first current is pulsed and the second current is pulsed. In one embodiment, the number of said pulses of the first current and of the second current is one or is greater than one.

In one embodiment, the pulse of the first current comprises a first sine wave and the pulse of the second current comprises a second sine wave such that the second sine wave lags by one quarter of a cycle behind the first sine wave.

In one embodiment, this invention provides a device for improved neuron excitation, the device comprising an electrode assembly comprising at least two pairs of electrodes. In one embodiment, the electrode assembly is used to generate a rotating electrical field. In one embodiment, at least two voltages are applied to the at least two pairs of electrodes in said electrode assembly. In one embodiment, the two voltages vary in time. In one embodiment, the at least two pairs of electrodes are at an angle with respect to each other. In one embodiment, the two pairs of electrodes are at a right angle with respect to each other and are perpendicular to each other.

In one embodiment, the voltages applied to the at least two pairs of electrodes, comprise: a first voltage applied to a first pair of electrodes and a second voltage applied to a second pair of electrodes such that the first voltage has a phase with respect to the second voltage. In one embodiment, the phase of the first voltage with respect to the second voltage is a 90 degree phase.

In one embodiment, the first voltage is pulsed and the second voltage is pulsed.

In one embodiment, the pulse of the first voltage comprises a first sine wave and the pulse of the second voltage comprises a second sine wave such that the second sine wave lags by one quarter of a cycle behind the first sine wave.

In one embodiment, the neuron excitation comprises axonal excitation. In one embodiment, the method is applied to a brain of a subject. In one embodiment, the method is applied for diagnostics. In one embodiment, the method is applied for treatment.

In one embodiment, the neuron excitation is applied to a neuron culture. In one embodiment, the response of the culture to the neuron excitation is detected.

In one embodiment, the rotating field excites the axons of the neurons, wherein the direction of the long axis of one axon creates a non-zero angle with respect to the direction of the long axis of a second axon.

In one embodiment, the rotating electric field excites at least the minimal number of neurons needed to generate a response in a neuron population, thereby generating an electrical response in the neuron population.

In one embodiment, the long axes of the axons of at least two of said neurons are not parallel.

In one embodiment, this invention provides a method for neuron excitation, the method comprising subjecting a neuron to a first electric field pulse longer than 200 µS in duration, thereby exciting the neuron.

In one embodiment, the first electric field pulse is equal to or longer than 1 ms in duration.

In one embodiment, the first electric field is induced by a magnetic field. In one embodiment, the magnetic field is induced by passing current through a coil. In one embodiment, the coil is connected to a capacitor. In one embodiment, the capacitor is at least a 1.0 mF capacitor.

In one embodiment, the pulse duration exceeds the electric field duration threshold needed to excite a dendrite or a dendrite population.

In one embodiment, this invention provides a device for dendrite excitation, the device comprising a capacitor connected to a coil and to a power supply, wherein the capacitance of said capacitor is at least 1.0 mF.

In one embodiment, the device generates an electric field pulse longer than 200 µS in duration, thereby exciting the dendrite. In one embodiment, the electric field pulse is equal to or longer than 1 ms in duration.

In one embodiment, the pulse duration exceeds the electric field duration threshold needed to excite a dendrite or a dendrite population. In one embodiment, dendrite excitation causes a neuron to fire.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 4 is a Table Summary of results for magnetic stimulation of 2D cultures. The threshold for activation is marked for each configuration of magnetic coils. Blank entries mark lack of an observable response to stimulation.

Figure 1:
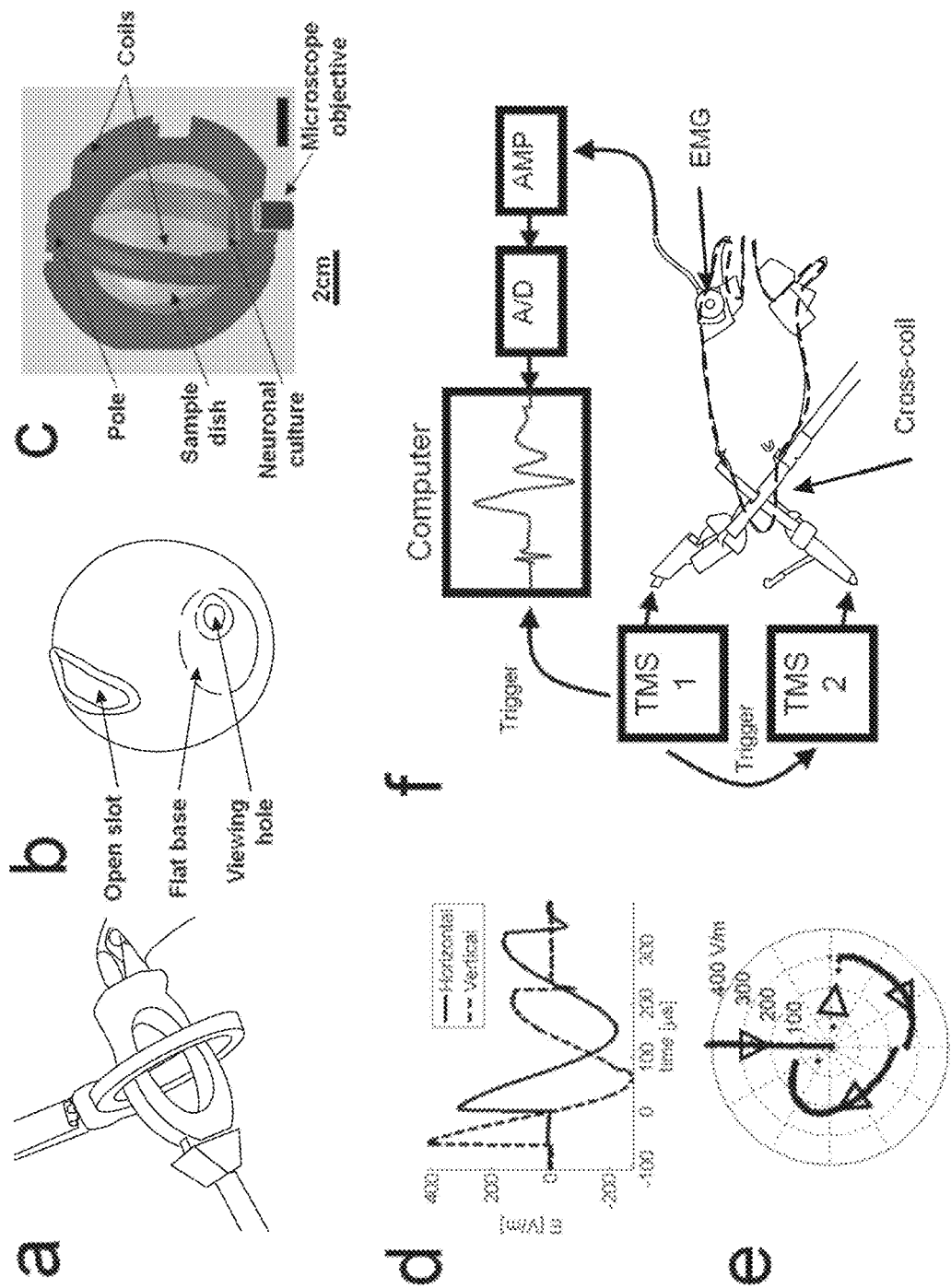
FIG. 1 shows embodiments of a cross-coil configuration; a) A picture of the actual coils used in the experiment. The two coils interlock on perpendicular planes and connect to two independent stimulators; b) A picture of the glass sphere that was custom made to fit inside the cross-coil. The glass coverslip and medium were inserted through a slot located at the top of the sphere. The coverslip lay on a flattened base at the sphere bottom and was viewed via a viewing hole, which was sealed with optically transparent glass. c) Schematic of the setup—the coverslip (bottom) was placed in a glass sphere inside the cross-coil while an inverted microscope monitored neuronal activity. all scale bars are 2 cm; d) The induced electric field in the cross-coil was measured using a pick-up coil oriented on the plane of one of the coils (termed horizontal plane coil, solid line) and on the plane of the second coil (termed vertical plane coil, dashed line). The Magstim stimulator was loaded to 100% and the HMS was loaded with 3.5 kV (see details in the methods section); e) A reconstruction of the effective electric field created from the sum of the two perpendicular components measured in a). The effective field was reconstructed for a specific location just inside the poles of the cross-coil (FIG. 1c). The effective field completes ¾ of a spiral cycle during the magnetic pulses cycle, as indicated by the black arrows; f) Cross-coil Setup for rat experiments. The rat's head was positioned inside the Cross-coil. EMG electrodes record muscle potentials from the Gastrocnemius. The EMG data was digitized and synchronized with the rotating field TMS (rfTMS) pulses to assess the motor response to rfTMS.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

A main limitation of TMS at this stage of its development is the highly specific directionality of the applied field, which demands a precisely targeted application that is extremely sensitive to motion and disturbances. Both location and orientation must be determined with high resolution and once an optimal position is determined, the magnet must be kept there during all the treatment.

The directional sensitivity arises because neurons are excited only if their axons are directed precisely along the induced electric field. This invention provides, in one embodiment, a technology that rotates the applied magnetic field, enabling the excitation of neurons whose axons are directed in many different directions.

The dependence on orientation arises because the magnetic stimulation of a neuron occurs at the axon, whose projection along the induced electric field is the relevant parameter for achieving excitation. Using quasi-one-dimensional patterned cultures, this invention provides a method to direct the axons to grow along rings concentric with the magnet, thus forcing them to have an extensive projection along the induced electric field in one embodiment. It should be noted that if it were possible to excite neurons by initiating an action potential in the dendrites then the situation would change, and the directionality would not be as crucial. Methods according to this aspect of the to invention are described herein below.

Another important feature that has been identified is that the initial excitation is achieved by stimulating a subpopulation of especially sensitive neurons, which then serve as a nucleating center for the firing of the whole network. In a culture that has been completely disconnected by applying receptor antagonists (CNQX, APV and Bicuculline), only this small subset (about 1 percent) is active and responds to magnetic stimulation. When the culture is connected, this kernel is responsible for eliciting a population response of all neurons in the network. If the size of the kernel is too small, the driving input into neurons in the network is not enough for initiating the population response.

To achieve a population response to magnetic stimulation, one must therefore excite action potentials in a large number of initiating neurons. In a neuronal network whose axonal orientation is random, this requirement is difficult to meet using conventional TMS, since the orientation of its induced field is constant and the probability that a large enough number of axons will be directed along this field is low.

Therefore, by inducing a rotating electric field whose orientation scans a wide range of angles during a single pulse, many axons could be excited all at once and the population response ensured. In the description below, methods to achieve such a rotation are described, and the resulting response of neuronal preparations is shown.

Magnetic Stimulation In-Vitro

As part of the investigation into the interaction of magnetic pulses with neurons, new capabilities and understanding of the parameters that determine the effective interaction of the magnetic pulse on the brain were developed. A combination of physical techniques and novel cell culturing methods is used to determine optimal parameters for the application of TMS. These parameters are largely spatial and geometric, pertaining to the shape of the neural substrate and the directionality of the magnetic field. In particular, it is now clear that the direction of axons must coincide with the direction of the electric field that is induced by the magnetic stimulation in order to maximize the effect of this stimulation.

Directionality, Rise Time and Cooperativity Limit the Effect of Magnetic Stimulation The neuro-physics of external field stimulation can be simplified using the passive cable equation (see A. L. Hodgkin, W. A. Rushton, Proc. Royal Soc. B 133, 444 (1946) and B. J. Roth, P. J. Basser, IEEE Trans Biomed. Eng. 37, 588 (1990)) which calculates the voltage that an external electric field induces on a cable's membrane (in this case the cable is a neurite) whose capacitance and resistance is known. This equation emphasizes the role of two relevant parameters in stimulating neurites. First, the neurons that respond strongest to the induced electric field are those whose neurite—axon or dendrite—lies parallel to the electric field. This observation is clear from theoretical considerations and has been the basis for obtaining the first ever magnetic stimulation of neurons from the central nervous system (CNS) using one-dimensional cultures. Second, neurites whose membrane rise time is much longer than the rise time of the external pulses will not respond to the stimulation. Since the rise time of commercial magnetic stimulators does not exceed 100 μs (one hundred microseconds) and the membrane rise time of dendrites is of the order of 1 ms (one millisecond)—excitation of neurons is almost exclusively initiated at the axon. A more detailed derivation can be found in A. Rotem and E. Moses, Biophys. J 94, 5065, 2008. Additionally, the collective response of a network of neurons either in the live brain or in-vitro cannot initiate from the firing of a single cell. Rather, it usually requires a critical number of initiating neurons that fire almost simultaneously in order to trigger a population burst that can be observed either in-vivo or in large neuronal cultures in-vitro. Details can be found in I. Breskin, J. Soriano, E. Moses, T. Tlusty, Phys. Rev. Lett. 97, 188102 (Nov. 3, 2006).

Figure 5:
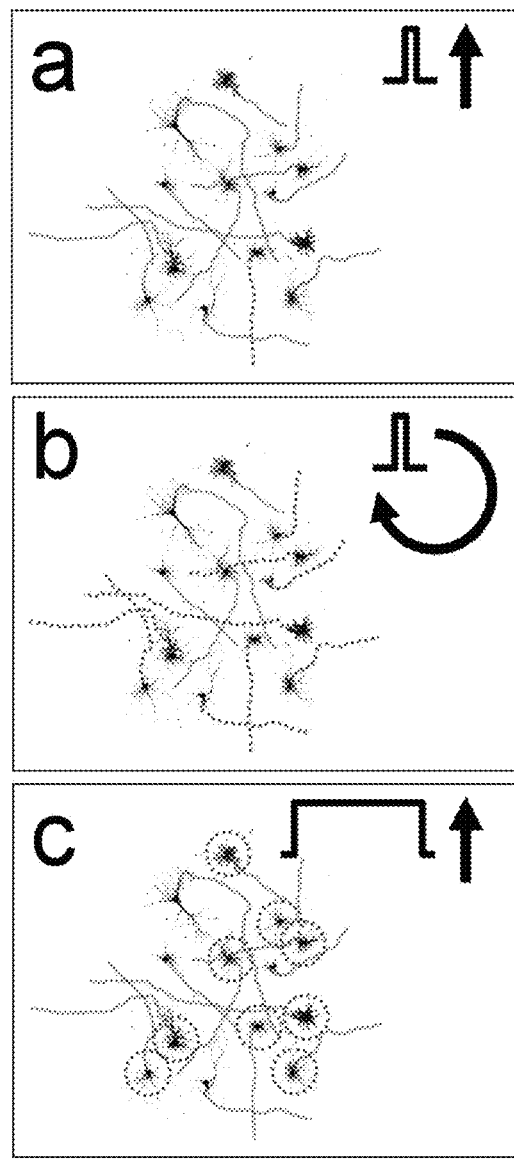
FIG. 5 is a schematic simulation of the stimulation of a culture whose cell's axons are randomly orientated. Each cell projects a single axon (solid or dashed lines) a) Applying a short magnetic pulse with a fixed single orientation (black arrow indicates direction of the electric field induced from the magnetic pulse). Only one cell whose axon (dashed line) is oriented parallel to the direction of the induced electric field is excited. b) Applying a short rotating magnetic pulse (arc indicates the span of rotation of the electric field induced from the magnetic pulse). All cells whose axons' orientations lie within the arc of the rotating electric field are excited, leading to a population response of the network. c) Applying a long magnetic pulse with a fixed orientation. All cells with dendrites oriented parallel to the direction of the induced electric field are excited (excited cells are marked with dashed circles), leading to a population response of the network.
Figure 6:
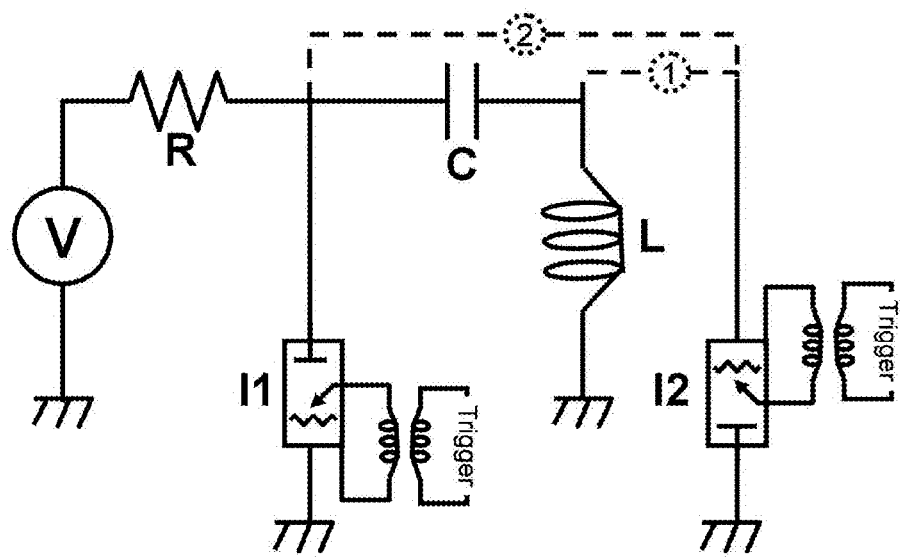
FIG. 6—a schematic diagram of one embodiment of the proposed device. The two ignitrons (I1 and I2) are triggered by a trigger generator. Connecting I2 via connection 1 results in a mono-polar pulse, while connecting it via connection 2 results in a bipolar pulse. I1 ignitron can be replaced with a thyristor, while I2 can be replaced by a diode.

The three factors mentioned above limit a successful magnetic stimulation of a network of neurons: they require that several neighboring cells in the network will have axons oriented parallel to the induced electric field. However, the direction of the magnetic field of a given coil is fixed, and so is the induced electric field. This means that in a network where neurons have randomly oriented axons the amount of neurons that can be excited is very small, not enough for a collective response of the network (FIG. 5a). This may be the main reason why it is so hard to excite two dimensional cultures in-vitro and cortical regions whose axonal orientation is not homogenous.

Rotating Electric Fields

In one embodiment, in order to overcome the problem caused by the anisotropy of axon orientation, time dependent electric field is employed, scanning through a whole range of angles. In one embodiment, this is obtained by using two coils, whose magnetic fields are perpendicular to each other and whose currents are phase shifted one from the other by a quarter of a cycle. The resulting electric field rotates in space during the pulse cycle, leading to the excitation of additional cells whenever it scans through their orientation. Since the cycle lasts no more than several hundred μsec (microseconds), all these cells are stimulated closely enough in time, ensuring a collective response of the network (FIG. 5b).

Rotating magnetic fields methods of this invention require the induction of a rotating field. It will be shown herein below how the induction of a rotating field is achieved, and that improved stimulating pulses of this invention target a larger number of neurons for excitation, both in the culture dish and in the live brain. These conceptually new tools may enable accessing areas in the brain that currently are not responsive to TMS, and provide easy excitation of two-dimensional cultures, which are more accessible as a model system than one-dimensional cultures. In one embodiment, such stimulating techniques will enable diagnostics of the brain and of components of the nervous system. In one embodiment, such stimulating methods will enable treatment of neurological conditions and other clinical conditions. In one embodiment, such stimulating techniques will be able to predict the onset of or the relative risk of a subject to develop a nervous-system related condition.

Dendritic Excitation.

In one embodiment, this invention provides a method to directly excite dendrites in the culture by applying pulses with durations of the order of 1 ms (1 millisecond). As opposed to axons, which usually project a long stretch at a single direction from the soma before branching, dendritic trees tend to branch extensively from the soma in an isotropous pattern. The option of directly exciting dendrites is thus extremely valuable since it overcomes the mentioned problem of directionality—each cell has numerous dendrites oriented in almost all possible directions and will respond to an induced field in a fixed direction (FIG. 5c). This solution may prove superior to the rotating field as it will enable targeting areas in the brain where all axons are oriented perpendicular to the cranial plane since the induced field can only be made to rotate in a plane parallel to the skull.

Theory—Increasing Rise Time of Magnetic Stimulation without Decreasing the Induced Electric Field.

Dendritic stimulation require pulse widths of the order of 1 ms. In order to obtain a given amplitude of induced electric field for a longer period of time, one needs to scale the magnetic field linearly with the pulse duration. This is because the induced electric field depends linearly on the time slope of the magnetic field, which decreases as the pulses get wider. For a given coil configuration discharged with a sinusoidal pulse with a given frequency w, the induced electric field E at some point is a function of the peak magnetic field B:

$$E = A\frac{\partial B(t)}{\partial t} = \frac{A\partial B_0 e^{iwt}}{\partial t} = iwAB \Rightarrow |E| \propto |wB|$$

With i the complex unit and the surface parameter $[A]=m^2$ takes into account the geometry of the problem. The peak amplitude of magnetic field is set by the capacitor parameters. The relation can be obtained from energy consideration since the energy stored in the capacitor prior to the discharge is theoretically equal to the energy of the magnetic field created by the coil:

$$\int_V \frac{B^2}{2\mu}dV = \frac{LI^2}{2} = \frac{CV^2}{2} \Rightarrow B \propto \sqrt{C}\,V$$

For a magnetic coil with an inductance L, the frequency w of a pulse discharged through the coil from a capacitor of capacitance C is given by:

$$w = 1/\sqrt{LC}$$

Combining the three relations above yields:

$$|E| \propto |wB| \propto \left|\frac{\sqrt{C}\,V}{\sqrt{LC}}\right| \propto \left|\frac{V}{\sqrt{L}}\right|$$

This analysis reveals the two pathways for increasing the pulse duration:

Increasing the inductance L: in this case one must also increase V quadratically with L to keep E constant. Increasing L means adding more turns to an already crowded coil system. Increasing the load V on the capacitor derives new infrastructure and safety measures that are adequate with higher voltages in the circuit.

Increasing the capacitance C: E is independent of C, so that increasing capacitance will increase the cycle time without side effects to deal with and is a preferred method for extending magnetic pulses.

In one embodiment, dendritic excitation methods require that electric field is applied for longer time periods. It will be shown herein below how the application of such electric fields is achieved, and that improved stimulating pulses of this invention target a larger number of neurons for excitation, both in the culture dish and in the live brain. These conceptually new tools may enable accessing areas in the brain that currently are not responsive to TMS, and provide easy excitation of two-dimensional cultures, which are more accessible as a model system than one-dimensional cultures. In one embodiment, such stimulating techniques will enable brain diagnostics. In one embodiment, such stimulating methods will enable treatment of neurological conditions and other clinical conditions.

In one embodiment, this invention provides a method for neuron excitation, the method comprising subjecting a neuron to a rotating electric field, thereby exciting the neuron.

In one embodiment, the rotating electric field is the sum of at least two time-dependent electric fields. In one embodiment, the at least two time-dependent electric fields are induced by at least two time-dependent magnetic fields. In one embodiment, the at least two time-dependent magnetic fields are induced by passing currents through at least two coils.

In one embodiment, the two coils are independently connected to two power supplies. In one embodiment, the two coils and the two power supplies are part of an apparatus. In one embodiment, the apparatus is part of a system.

In one embodiment, the system further comprises an electrical signal detection unit, an imaging unit or a combination thereof. In one embodiment, the two coils are perpendicular to each other.

In one embodiment, the currents passed through the at least two coils comprise: a first current passed through a first coil and a second current passed through a second coil such that the first current has a 90 degree phase with respect to the second current. In one embodiment, the 90 degree phase represents a lag of 1 quarter of a cycle of the first current behind the second current.

In one embodiment, the first current is pulsed and the second current is pulsed. In one embodiment, the pulses of the first current and of the second current are of the same pulse rate. In one embodiment, the pulses of the first current and of the second current are of the same wave pattern. In one embodiment, the pulses of the first current and of the second current are of the same peak amplitude. In one embodiment, the number of the pulses of the first current and of the second current is one. In one embodiment, the number of the pulses of the first current and of the second current is greater than one.

In one embodiment, the pulse pattern comprises: the number of pulses, the time of each pulse, the time between pulses or a combination thereof.

In one embodiment, the pulse of the first current comprises a first sine wave and the pulse of the second current comprises a second sine wave such that the second sine wave lags by one quarter of a cycle behind the first sine wave. In one embodiment, the pulse of the first current comprises one period of the first sine wave and the pulse of the second current comprises one period of the second sine wave.

In one embodiment, this invention provides a method for neuron excitation, the method comprising subjecting a neuron to a rotating electric field, thereby exciting the neuron and collecting or detecting an electric signal from the excited neuron. In one embodiment, collecting or detecting an electric signal from the neuron is done by Electroencephalography (EEG).

In one embodiment, the rotating electrical field is generated using an electrode assembly. In one embodiment, voltage is applied to the electrode assembly. In one embodiment, the voltage varies in time. In one embodiment, the electrode assembly is rotating in space.

In one embodiment, the neuron excitation comprises axonal excitation.

In one embodiment, the method is applied to a brain of a subject. In one embodiment, the method is applied for diagnostics. In one embodiment, the method is applied for treatment. In one embodiment, the neuron excitation is applied to a neuron culture. In one embodiment, the response of said culture to the neuron excitation is detected. In one embodiment, the response is detected by imaging spectral changes in the culture. In one embodiment, the response is detected by fluorescence.

In one embodiment, the rotating field excites the axons of the neurons, wherein the direction of the long axis of one axon creates a non-zero angle with respect to the direction of the long axis of a second axon. In one embodiment, the rotating electric field excites at least the minimal number of neurons needed to generate a response in a neuron population, thereby generating an electrical response in the neuron population. In one embodiment, the long axes of the axons of at least two of the neurons are not parallel.

In one embodiment, this invention provides a device for improved neuron excitation, said device comprising a set of at least two separate coils. In one embodiment, the at least two separate coils are driven with shifted phases of current in time. In one embodiment, the coils create at least two time-dependent electric fields, whose resultant sum changes orientation in time. In one embodiment, the two coils are independently driven. In one embodiment, the two coils are independently driven by two power supplies.

In one embodiment, the two coils are at an angle with respect to each other. In one embodiment, the two coils are at a right angle with respect to each other and are perpendicular to each other.

In one embodiment, the currents passed through the at least two coils comprise: a first current passed through a first coil and a second current passed through a second coil such that the first current has a phase with respect to the second current. In one embodiment, the phase of the first current with respect to the second current is a 90 degree phase.

In one embodiment, the first current is pulsed and the second current is pulsed. In one embodiment, the number of said pulses of the first current and of the second current is one or is greater than one.

In one embodiment, the pulse of the first current comprises a first sine wave and the pulse of the second current comprises a second sine wave such that the second sine wave lags by one quarter of a cycle behind the first sine wave.

In one embodiment, this invention provides a device for improved neuron excitation, the device comprising an electrode assembly comprising at least two pairs of electrodes. In one embodiment, the electrode assembly is used to generate a rotating electrical field. In one embodiment, at least two voltages are applied to the at least two pairs of electrodes in said electrode assembly. In one embodiment, the two voltages vary in time. In one embodiment, the at least two pairs of electrodes are at an angle with respect to each other. In one embodiment, the two pairs of electrodes are at a right angle with respect to each other and are perpendicular to each other.

In one embodiment, the voltages applied to the at least two pairs of electrodes, comprise: a first voltage applied to a first pair of electrodes and a second voltage applied to a second pair of electrodes such that the first voltage has a phase with respect to the second voltage. In one embodiment, the phase of the first voltage with respect to the second voltage is a 90 degree phase.

In one embodiment, the first voltage is pulsed and the second voltage is pulsed.

In one embodiment, the pulse of the first voltage comprises a first sine wave and the pulse of the second voltage comprises a second sine wave such that the second sine wave lags by one quarter of a cycle behind the first sine wave.

In one embodiment, the neuron excitation comprises axonal excitation. In one embodiment, the method is applied to a brain of a subject. In one embodiment, the method is applied for diagnostics. In one embodiment, the method is applied for treatment.

In one embodiment, the neuron excitation is applied to a neuron culture. In one embodiment, the response of the culture to the neuron excitation is detected.

In one embodiment, the rotating field excites the axons of the neurons, wherein the direction of the long axis of one axon creates a non-zero angle with respect to the direction of the long axis of a second axon.

In one embodiment, the rotating electric field excites at least the minimal number of neurons needed to generate a response in a neuron population, thereby generating an electrical response in the neuron population.

In one embodiment, the long axes of the axons of at least two of said neurons are not parallel.

In one embodiment, this invention provides a method for neuron excitation, the method comprising subjecting a neuron to an electric field pulse longer than 200 μS in duration, thereby exciting the neuron. In one embodiment, the electric field pulse is equal to or greater than 1 ms in duration. In one embodiment, the method further comprises collecting or detecting an electric signal from the neuron. In one embodiment, collecting or detecting an electric signal from the neuron is done by Electroencephalography (EEG).

In one embodiment, the electric field is induced by a magnetic field. In one embodiment, the magnetic field is induced by passing current through a coil.

In one embodiment, the coil is connected to a capacitor. In one embodiment, the capacitance of the capacitor is at least 1.0 mF. In one embodiment, the capacitance is a result of said capacitor material, capacitor geometry, capacitor's dimensions or a combination thereof.

In one embodiment, the electric field pulse duration exceeds the electric field duration threshold needed to excite a dendrite or a dendrite population. In one embodiment, the neuron excitation comprises dendrite excitation.

In one embodiment, this invention provides a device for dendrite excitation, the device comprising a capacitor connected to a coil and to a power supply, wherein the capacitance of said capacitor is at least 1.0 mF.

In one embodiment, the device generates an electric field pulse longer than 200 μS in duration, thereby exciting said dendrite. In one embodiment, the electric field pulse is equal to or longer than 1 ms in duration.

In one embodiment, the pulse duration exceeds the electric field duration threshold needed to excite a dendrite or a dendrite population. In one embodiment, dendrite excitation causes a neuron to fire.

Definitions

In one embodiment, neurons are responsive cells in the nervous system that process and transmit information by electrochemical signaling. In one embodiment, neuron excitation can be done by inducing or by changing an electric field on or on the surroundings of a neuron, or parts of the neuron. In one embodiment, induced electric field or change in electric field on a neuron membrane on or a small area or region of the neuron membrane may cause neuron excitation. In one embodiment, a rotating electric field is an electric field wherein the direction of the field changes or varies in time/space. In one embodiment, a rotating electric field has a plurality of field components the direction of each is rotating in space. In one embodiment, a rotating electric field has a plurality of field components the direction of each is rotating in space as a function of time.

In one embodiment, a rotating magnetic field has a plurality of field components the direction of each fixed and whose amplitude changes in time. In one embodiment, a rotating magnetic field has a plurality of field components the direction of which is fixed and whose amplitude varies as a function of time.

In one embodiment, a time-dependent electric field is an electric-field wherein the magnitude and direction of the field varies with time. In one embodiment, current is an electrical current. In one embodiment, a coil is an electrically conducting coil. In one embodiment a coil is an electrically conducting material, wire or plate of a circular, rounded or a spiral-like structure, through which an electrical current may be made to pass.

In one embodiment, two coils in devices of this invention are independently connected to two power supplies such that each power supply operates independently, and such that voltage/current are induced independently in each coil. In one embodiment, one power supply with a plurality of outputs operates the at least two coils.

In one embodiment, an electrical signal detection unit, an imaging unit or a combination thereof comprise an Electroencephalography (EEG) unit, a magnetic resonance imaging (MRI) unit or a combination thereof.

In one embodiment, the two coils are perpendicular to each other. In one embodiment, the two coils are close to being perpendicular to each other. In one embodiment, the angle between the planes of the coils ranges between 80 degrees and 100 degrees.

In one embodiment, a 90 degree phase of one current with respect to another current represents a quarter of a period delay of a periodic current function of one current with respect to a similar periodic function of another current. According to this embodiment, a full period of a current function is represented by 360 degrees. In one embodiment, the 90 degree phase represents a lag of 1 quarter of a cycle of said first current behind the second current. In one embodiment, one cycle is one period of a periodic function.

In one embodiment, the waveform formula for a rotating electric field induced by two magnetic fields induced by two coils is described as follows: one coil starts discharging and ¼ of a cycle later, the second coil starts discharging. The resulting electric field of the first coil is: $A*\cos(2*pi*t/T)$ where T is the cycle period, and A the amplitude. The resulting field of the second coil is: $A*\cos(2*pi*t/T-pi/2)$. If the two electric fields are perpendicular to one another, equal in peak amplitude and in cycle time, then the resulting sum of two fields performs a rotation of 270 deg.

In one embodiment, pulsed current is a current that is introduced to a coil in pulses. In one embodiment, during a pulse, current passes through a coil and in an interval between pulses, no current or very minimal current passes through the coils. In one embodiment, the minimal current that may pass through the coil in an interval between pulses is below a threshold needed to produce an effective magnetic field for methods of this invention. In one embodiment, current frequency is the frequency of the alternating current passed through coils of this invention. In one embodiment, wave pattern is the pattern of the current function. In one embodiment, the wave pattern is the current vs. time function. In one embodiment, current amplitude, peak amplitude represents the value of the current or the highest value of the current passed through coils of this invention. In one embodiment, pulse pattern is defined by the number of current pulses, the time of each current pulse, the time between current pulses or a combination thereof.

In one embodiment, the waveform of the current is a sine wave. In one embodiment, the phase between the two currents passed in two different coils can be represented by a sine wave for the first current and by a cosine wave for the second current.

In one embodiment, an electrode assembly comprises at least two electrodes. In one embodiment, by applying voltage to the at least two electrodes, an electric field is generated in the area between the electrodes. In one embodiment, by changing the position of the electrodes, or by applying voltage to three or more electrodes, a rotating electric field may be generated in the area between the electrodes or in parts of the area between the electrodes.

In one embodiment, voltage is electrical voltage. In one embodiment, the term capacitance is the term used in electromagnetism and in electronics. In one embodiment, capacitance is the ability of a body to hold an electrical charge.

In one embodiment, high capacitance is any value of capacitance in the range of 50-400 μF for the axonal excitation field or any value of capacitance larger than 1 mF for the dendritic excitation.

In one embodiment, dendrites are the branched projections of a neuron that act to conduct the electrochemical stimulation received from other neural cells to the cell body, or soma, of the neuron from which the dendrites project. Electrical stimulation is transmitted onto dendrites by upstream neurons via synapses which are located at various points throughout the dendritic arbor. Dendrites play a critical role in integrating these synaptic inputs and in determining the extent to which action potentials are produced by the neuron. In one embodiment, an axon is a long, slender projection of a nerve cell, or neuron that conducts electrical impulses away from the neurons cell body or soma.

In one embodiment, a neurite refers to any projection from the cell body of a neuron. This projection can be either an axon or a dendrite. In one embodiment, action potential is a self-regenerating wave of electrochemical activity that allows nerve cells to carry a signal over a distance. In one embodiment, action potential is the primary electrical signal generated by nerve cells, and it arises from changes in the permeability of the nerve cell's axonal membranes to specific ions. In one embodiment, action potentials (also known as nerve impulses or spikes) are pulse-like waves of voltage that travel along several types of cell membranes. In one embodiment, firing of a neuron, a neuron that fire, or the term "fire", "firing" or to "fire" means the event of an action potential occurring in the so mentioned neuron.

Dimensions and Values

In one embodiment, the following parameters determine the magnetic pulse amplitude and cycle time: voltage load on the capacitor, coil inductance L and capacitor capacitance C.

In one embodiment, the voltage load V on the capacitor ranges between 0 V and 5 kV. In one embodiment, the voltage load V on the capacitor can be made to load up to 20 kV. In one embodiment, the coil inductance L ranges between 0 μH and 50 μH. In one embodiment, the coil inductance L ranges between 1 μH and 50 μH. In one embodiment, the capacitor capacitance is 109 μF. In one embodiment, for dendritic excitation, the capacitor capacitance is 1 mF. In one embodiment, for dendritic excitation, the capacitor capacitance is 5 mF. In one embodiment, the capacitor capacitance ranges between 1 mF and 5 mF.

In one embodiment, the resulting cycle times (or pulse width) from these parameters ranges between 100 μsec and 5 msec.

In one embodiment, stimulators used in methods of this invention comprise voltage sources, capacitors and coils with the following parameters: V=0-5 kV, L=10-50 μH, C=109 μF and resulting cycle times are of 200 μsec-500 μsec.

In one embodiment, the stimulators comprising the coils can be used for single TMS or for multiple TMS with stimulation rates of up to 100 Hz. The orientation of the coils with respect to the (culture) dish, animal, or human subject can be changed.

In one embodiment, the strength of the electric field used to excite a neuron or a neuron assembly ranges between 50-500V/m. In one embodiment, the strength of the electric field used is at least 100V/m.

In one embodiment, the magnetic field strength used to generate the first rotating electric field ranges between 0.1-5 T. In one embodiment, the strength of the electric field used is at least 100V/m.

In one embodiment, the current passed through the coils ranges between 1 kA-10 kA. In one embodiment, the current passed through the coils is at least 1 kA.

In one embodiment, the current passed through a first coil and the current passed through a second coil have a 90 degree phase with respect to each other. In another embodiment, the current phase ranges between 85 and 95 degrees. In another embodiment, the current phase ranges between 1 and 90 degrees. In one embodiment, the current phase ranges between 90 and 180 degrees. In one embodiment, the current phase ranges between 180 and 270 degrees. In one embodiment, the current phase ranges between 270 and 359 degrees. In one embodiment the current phase is any number of degrees other than zero degrees. In one embodiment, current phases in degrees refer to currents exhibiting certain periodical function of the current vs. time. In one embodiment, the periodic function of the current vs. time is represented by a sine wave. In one embodiment, any other phase and waveform function combination may be useful to create a rotating field that is not circular (e.g. elliptical or any arbitrary near circular form that may be advantageous for a specific instance of neurons).

In one embodiment, the 90 degree phase represents a lag of 1 quarter of a cycle of said first current behind said second current. In one embodiment, the cycle lag ranges between 0.20 of a cycle and 0.30 of a cycle. In one embodiment, the cycle lag ranges between 0.01 of a cycle and 0.50 of a cycle. In one embodiment, the cycle lag ranges between 0.50 of a cycle and 0.99 of a cycle. In one embodiment, cycle lag refer to the lag of one current behind another current wherein both currents exhibit a certain periodical function of the current vs. time. In one embodiment, the periodic function of the current vs. time is represented by a sine wave.

In one embodiment, only one pulse of two currents in two coils is used. In another embodiment, more than one pulse is used. In one embodiment, the current pulses in the at least two coils are of the same pulse frequency. In another embodiment, current pulses in the at least two coils are of a different pulse frequency. In one embodiment, pulse frequency is 1 Hz. In one embodiment, pulse frequency is 50 Hz. In one embodiment, pulse frequency ranges between 1 Hz and 50 Hz. In one embodiment, pulse frequency ranges between 1 Hz and 100 Hz.

In one embodiment, the pulses of the first current and the pulses of the second current are of the same wave pattern. In one embodiment, the pulses are of a different wave pattern. In one embodiment, any pulses waveform combination may be useful to create a rotating field that is not circular (e.g. elliptical or any arbitrary near circular form that may be advantageous for a specific instance of neurons).

In one embodiment, the currents peak amplitude ranges between 1 kA-10 kA.

In one embodiment, the number of pulses used for a specific stimulation event is one. In one embodiment, the number of pulses used for a specific stimulation event ranges between 1 and 50. In one embodiment, the number of pulses used for a specific stimulation event ranges between 1 and 100. In one embodiment, the number of pulses used for a specific stimulation event ranges between 100 and 1000.

In one embodiment, the time of each pulse ranges between 1 microsecond and 100 microseconds. In one embodiment, the time of each pulse ranges between 10 microsecond and 100 microseconds. In one embodiment, the time of each pulse ranges between 50 microsecond and 100 microseconds. In one embodiment, the time of each pulse ranges between 100 microsecond and 200 microseconds. In one embodiment, the time of each pulse ranges between 100 microsecond and 1000 microseconds. In one embodiment, the time of each pulse ranges between 100 microsecond and 500 microseconds. In one embodiment, the time of each pulse ranges between 100 microsecond and 2000 microseconds. In one embodiment, the time of each pulse ranges between 1 millisecond and 10 milliseconds. In one embodiment, the time of each pulse ranges between 1 millisecond and 5 milliseconds.

In one embodiment, the time between pulses is approximately 20 milliseconds. In one embodiment, the time between pulses ranges between 10 millisecond and 30 milliseconds. In one embodiment, the time between pulses is 1 millisecond. In one embodiment, the time between pulses ranges between 1 millisecond and 10 milliseconds. In one embodiment, the time between pulses ranges between 10 millisecond and 100 milliseconds. In one embodiment, the time between pulses ranges between 100 µS and 30 seconds. In one embodiment, the time between pulses is of the order of seconds. In one embodiment, the time between pulses is of the order of milliseconds. In one embodiment, the time between pulses is of the order of microseconds.

In one embodiment, one current pulse passed through one coil comprises one period of a sine wave and the second current pulse passed through a second coil comprises one period of a cosine wave. In one embodiment, the current pulses comprises half a period of a sine wave. In one embodiment, the current pulses comprise a quarter of a period of a sine wave. In one embodiment, the current pulses comprise three quarters of a period of a sine wave. In one embodiment, the current pulse comprises two periods of the sine wave. In one embodiment, the current pulses comprise between 1 and 10 periods of the sine wave. In one embodiment, the current pulses comprises between 0.01 and 0.99 of a period of a sine wave.

In one embodiment, the voltage applied to the electrode assembly ranges between 1 and 36 V peak to peak. In one embodiment, the pulse is a bi-polar square pulse. In one embodiment, the pulse width ranges between 0.1 and ten milliseconds.

In one embodiment, the voltage applied to certain electrodes in an electrode assembly varies in time. In one embodiment, the voltage variation in time is different along different directions or along different axes, such that region(s) between the electrodes to which the voltage is applied experience variations in electric field.

In one embodiment, the electrode assembly rotates in space. In one embodiment, the electrode assembly or part of it rotates by 90 degrees. In one embodiment, the electrode assembly is capable of rotating by 180 degrees. In one embodiment, the electrode assembly is capable of rotating by 360 degrees or less.

In one embodiment, this invention provides a method for neuron excitation, the method comprising subjecting a neuron to a first electric field pulse greater than 100 µS in duration, thereby exciting the neuron.

In one embodiment, the electric field pulse duration is equal to or greater than 1 ms in duration. In one embodiment, the pulse duration or rise time ranges between 100 µS and 1000 µS. In one embodiment, the pulse duration or rise time ranges between 750 µS and 1250 µS. In one embodiment, the pulse duration or rise time ranges between 1 ms and 10 ms. In one embodiment, the pulse duration or rise time ranges between 0.5 ms and 2 ms. In one embodiment, the pulse duration or rise time ranges between 0.9 ms and 100 ms.

In one embodiment, the capacitance of the capacitor connected to the coil is at least 0.1 mF. In one embodiment, the capacitance of the capacitor connected to the coil is at least 1.0 mF. In one embodiment, the capacitance of the capacitor connected to the coil is at least 4.8 mF. In one embodiment, the capacitance of the capacitor connected to the coil is at least 1.0 mF. In one embodiment, the capacitance of the capacitor connected to the coil is at least 0.05 mF. In one embodiment, the capacitance of the capacitor connected to the coil ranges between 0.1 mF and 10 mF. In one embodiment, the capacitance of the capacitor connected to the coil ranges between 1 mF and 5 mF. In one embodiment, the capacitance of the capacitor connected to the coil ranges between 10 mF and 50 mF.

In one embodiment, the coil number of turns ranges between 20 and 80 turns. In one embodiment, the coil number of turns ranges between 10 and 50 turns. In one embodiment, the coil number of turns ranges between 10 and 100 turns. In one embodiment, the coil number of turns ranges between 40 and 100 turns.

In one embodiment, the coil inductance L ranges between one and 50 pH. In one embodiment, the coil inductance L ranges between one and 10 pH. In one embodiment, the coil inductance L ranges between 25 and 50 pH.

In one embodiment, the coil inner/outer diameter is 100 mm. In one embodiment the coil inner/outer diameter is 10 mm. In one embodiment the coil inner/outer diameter ranges between 5 mm and 200 mm. In one embodiment the coil inner/outer diameter ranges between 10 mm and 50 mm. In one embodiment the coil inner/outer diameter ranges between 50 mm and 100 mm. In one embodiment the coil inner/outer diameter ranges between 100 mm and 200 mm.

In one embodiment, the coil is made of a conducting material. In one embodiment, the coil is made of metal. In one embodiment, the coil is made of copper. In one embodiment, the coil is made of insulated copper wire. In one embodiment, the copper wire thickness is 0.01" (0.254 mm) and 0.25" (6.35 mm) wide. In one embodiment, the coil wire thickness, width or diameter ranges between 0.005" (0.127 mm) and 0.50" (12.7 mm).

In one embodiment, the stimulator comprises a capacitor of 4.8 mF and a maximum voltage load of 6.5 kV. In one embodiment, the stimulator comprises a capacitor of 0.1 mF and a maximum voltage load of 22 kV.

In one embodiment, magnetic fields generated by methods of this invention ranges between 0 and 1 Tesla. In one embodiment, magnetic fields generated by methods of this invention ranges between 1 and 10 Tesla. In one embodiment, magnetic fields generated by methods of this invention ranges between 0.5 and 1.5 Tesla. In one embodiment, magnetic fields generated by methods of this invention ranges between 0.2 and 3 Tesla.

In one embodiment, the stimulating threshold of the electric field used in methods of this invention, ranges between 200 V/m and 1000 V/m for cultures excited by a two-coil induced rotating electric field. In one embodiment, the electric field generated by a two-coil configuration in methods of this invention, ranges between 1 V/m and 200 V/m. In one embodiment, the stimulating threshold of potential ranges between 1 and 20 V/m for cultures excited by an electrode assembly.

In one embodiment, the unit ms means milliseconds. In one embodiment, µs means microsecond(s). In one embodiment mF means millifarad. In one embodiment, pH means microHenry. In one embodiment, all units describing physical parameters are the conventional units used and recognized by any person skilled in the art.

Geometries and Orientations

In one embodiment, the coil is spherical. In one embodiment, the coil has a FIG. 8 shape. In one embodiment the coil is of a clover-leaf shape. In one embodiment, the coil is of a butterfly shape. In one embodiment, two coils are employed. In one embodiment, three or four coils are employed. In one embodiment, five or six coils are used. In one embodiment, the number of coils ranges between two and ten coils. In one embodiment, the number of coils ranges between three and five coils. In one embodiment, the number of coils ranges between six and 20 coils. In one embodiment, each coil plane is perpendicular to all other coil planes. In one embodiment, all coil planes lie in the same plane. In one embodiment, there is an angle other than 90 degrees between the planes of at least two coils. In one embodiment, a multitude of protocols may be used to extend the rotating fields. Any combination of two separate coil systems can be combined to create some variation of a rotating electric field, for example an elliptical rotation instead of perfect circular one. The amplitude of both coils need not be the same, and so doesn't the cycle time and the relative orientation between the two coils.

Materials

In one embodiment, the coil is a wire made of metal. In one embodiment, the metal is copper. In one embodiment, the inner volume of the coil is filled with a magnetic material. In one embodiment, the inner volume of the coil is filled with iron. In one embodiment, the coil conducting wire is insulated. In one embodiment, the coil comprises turns. In one embodiment, the electrodes are made of metal. In one embodiment, the metal comprises platinum, gold or palladium. In one embodiment, the electrodes are made of silver. In one embodiment, the coil is surrounded by a cooling system. In one embodiment, the cooling system prevents the coil from over-heating while in operation.

Methods

In one embodiment, this invention provides high efficiency excitation of axons, thereby making a neuron fire. This is achieved by scanning all or most of the directions of the desired axon population (axons are directional) with an electric field. In one embodiment, this is achieved by creating a rotating electric field that scans all these directions and can excite the axons regardless of their directionality. This involves a device having two coils configured at an angle (e.g. perpendicular) to each other, each connected separately to a different source of current/power, the two coils driven at a phase shift in time with respect to each other. The phase shift causes the electric field to scan over time, different directions in space.

In one embodiment, this invention provides a method for exciting the dendritic tree of neurons, thereby making the neurons fire. In one embodiment, this method involves the application of only one electric field, whose spatial direction is not crucial—neurons have multiple dendrites, which branch out in all directions. In one embodiment, as long as the field is directed in a good general direction, it will excite dendrites and does not need to be rotated. According to this aspect and in one embodiment, the device is based on the design of a special power supply, with a very large capacitor, delivering a very long pulse (five times longer than conventional TMS stimulators in one embodiment).

In one embodiment, methods of this invention are used In vitro. In one embodiment, methods of this invention are used In vivo. In one embodiment, methods of this invention are used on cell cultures. In one embodiment, methods of this invention are used on two-dimensional cell cultures. In one embodiment, methods of this invention are used on three-dimensional cell cultures. In one embodiment, methods of this invention are used on very small cell cultures. In one embodiment, at least one dimension describing the size of the cell culture used in methods of this invention ranges between 1 and 20 micrometers. In one embodiment, when a rotating field method or a dendritic excitation method of this invention are applied to a culture in a dish, the size of the dish the size of the coverslip on which the culture is grown/deposited and the culture coverslip patterning methods are adjusted to fit the stimulators and stimulator parameters in order to achieve neuronal excitation of neurons in the culture. In one embodiment, methods of this invention are used on animals. In one embodiment, methods of this invention are used on human subjects.

In one embodiment, this invention provides a TMS tool which performs TMS according to methods of this invention. In one embodiment, an apparatus is designed such that the apparatus or elements in the apparatus may perform TMS according to methods of this invention. In one embodiment, this invention provides systems for TMS. In one embodiment, TMS systems of this invention perform TMS according to methods of this invention. In one embodiment, this invention provides a kit comprising a TMS tool working according to methods of this invention.

In one embodiment, methods or certain elements in methods of this invention are performed automatically. In one embodiment, methods or elements in methods of this invention are performed by a robot. In one embodiment, systems of this invention operating by methods of this invention are designed for home-use by a subject.

In one embodiment, the devices, tools, apparatuses or systems of this invention further comprises stands, supports and/or other accessories for holding the coils or the electrode assembly in desired positions with respect to the subject, the animal or the culture being probed. In one embodiment, the coils, the electrodes, the devices, tools, apparatuses or systems of this invention further comprises moving parts for helping in positioning the coils or the electrodes with respect to the area under examination or the area treated. In one embodiment, the moving parts are controlled by a computerized system.

In one embodiment, methods of this invention further comprise collecting or detecting signal from neurons. In one embodiment, detecting or collecting a signal from the brain is done by EEG and/or MRI. In one embodiment, detecting or collecting a signal from the brain is done by motor feedback i.e. the activation of muscles by recording with EMG or by watching for movement. In one embodiment, detecting or collecting a signal from the brain is done by human feedback, e.g. reporting visual perception (phosphenes) or any other sensation, In one embodiment, the time scale of the magnetic pulse used for dendritic excitation performed by methods of this invention exceed 250 microseconds. In one embodiment, the time scale of the magnetic pulse used for dendritic excitation performed by methods of this invention exceed 500 microseconds. In one embodiment, the time scale of the magnetic pulse used for dendritic excitation performed by methods of this invention exceed 1000 microseconds.

In one embodiment, devices and tools provided by this invention are designed and operate to fulfill the need for dendritic excitation which in turn needs long pulse times. In one embodiment, the design of devices for a longer time of neuron excitation demands a relatively large capacitor, and such capacitor is provided in devices of this invention as described herein.

In one embodiment, detecting or collecting a signal in-vitro is performed by electrophysiology (electrodes) or by optical imaging of activity—calcium imaging, voltage sensitive dyes imaging, etc.

In one embodiment, an electrode assembly is used to generate the rotating electric field. In one embodiment, electric excitation is done using at least two pairs of independent electrodes. In one embodiment, a first sine wave is applied to one pair of electrodes and a second sine wave that is 90 deg apart from the first sine wave is applied to the second pair of electrodes. In one embodiment, the two pairs of electrodes are perpendicular to each other.

In one embodiment, methods and tools of this invention are used for diagnosing and/or for treating neurological-related diseases and conditions. In another embodiment, methods and tools of this invention are used for diagnosing the risk of acquiring a neurological-related condition or disorder. In another embodiment, methods and tools of this invention are used for treating subjects having a risk of acquiring a neurological-related condition or disorder.

In one embodiment, the conditions treated and/or diagnosed by methods of this invention comprise cognitive diseases or disorders. In some embodiments, the cognitive disease or disorder comprises impaired memory, learning disorder, Alzheimer's disease, multi-infarct dementia, including the Lewy-body variant of Alzheimer's disease, multi-infarct dementia, Parkinson's disease; Creutzfeld-Jakob disease, Korsakow's disorder, ischemia, stroke, head trauma, hypoglycemia, carbon monoxide poisoning, lithium intoxication, vitamin (B 1, thiamine and B 12) deficiency, depressive disorder, after electro-convulsive therapy (ECT), or others as will be appreciated by the skilled artisan.

In some embodiments, the systems and methods of this invention may be utilized to diagnose mild cognitive disorder or more severe neuropsychiatric conditions, cognitive diseases or disorders, to distinguish between them, or in some embodiments, to indicate a likelihood or timing of progression of the former to the latter.

In one embodiment, the mild cognitive disorder can comprise, for example, Mild Cognitive Impairment (MCI) (which herein, includes cognitive impairments ranging from minimal to mild), mild memory loss, age associated memory impairment (AAMI), age related cognitive decline (ARCD), Benign Senescent Forgetfulness (BSF), or Cognitive Impairment No Dementia (CIND). A mild cognitive disorder includes disorders that require cognitive impairment as a clinical feature of the syndrome and subjects do not meet diagnostic criteria for dementia, e.g., DSM-IV TR criteria for dementia. Among these disorders, mild cognitive impairment is a condition characterized by cognitive, most commonly memory, deficits in the absence of clinically significant functional impairment. In one embodiment, the invention provides methods for predicting whether a subject who has MCI is likely to develop Alzheimer's disease.

Methods and systems of this invention can be used in conjunction with additional clinical tests and/or with additional clinical evaluation or treatment methods and tools. Such combination of methods may be used for assessing, diagnosing or determining a neurological condition in a subject. Such combination of methods and tools can be used for assessing or determining the probability or relative risk that a subject has for developing a neuropsychiatric condition, cognitive disease or disorder. Such combination of methods or tools can be used for the treatment of a subject having or suffering from a disorder such as any of the disorders listed herein above and below. Such combination of methods or tools can be used for the treatment of a subject having a relative risk for developing a neuropsychiatric condition, cognitive disease or disorder such as any of the disorders listed herein above and below.

Such additional clinical tests or evaluation methods are but not limited to neuropsychological tests of memory and other cognitive abilities, tests of ability to perform daily functional activities, brain imaging tests (including MRI (magnetic resonance imaging), SPECT (single photon emission computerized tomography), and PET (positron emission tomography)), and tests of biomarkers in blood, cerebrospinal fluid and other bodily fluids and tissues. EEG, linguistic tests, sensory system responses tests for vision, hearing, somatic sensation (touch), taste and olfaction (smell) responses. Gross and fine motor skills tests etc. In one embodiment, imaging methods involve the detection of fluorophores. In one embodiment, fluorophores or other biomarkers are administered to the subject or to a cell culture before or in parallel to performing TMS on the subject using methods of this invention. In one embodiment, administration of a fluorophore or other biomarker to a subject is an oral, intravenous, intraarterial, intramuscular, intracranial, intranasal, subcutaneous, parenteral, transmucosal, transdermal, or topical administration. In one embodiment, a subject's pulse, heart rate and temperature are measured in conjunction with magnetic stimulation methods described by this invention.

In one embodiment, drugs are administered prior to or in conjunction with performing TMS methods of this invention on a subject or on a culture. In one embodiment, administration of drugs to a subject is an oral, intravenous, intraarterial, intramuscular, intracranial, intranasal, subcutaneous, parenteral, transmucosal, transdermal, or topical administration.

TMS methods described herein maybe used in conjunction with traditional TMS methods. TMS methods described herein maybe used prior to, in parallel or subsequent to conventional TMS methods.

The neuropsychiatric condition, cognitive disease or disorder which may be ascertained and/or treated by the systems/methods of this invention include, but are not limited to, Alzheimer's disease, Parkinson's disease, Huntington's disease, Korsakoffs amnestic syndrome, acquired immunodeficiency syndrome (AIDS), amyotrophic lateral sclerosis, motor neuron disease, depression, schizophrenia, advanced anorexia, frontotemporal dementia, lewy body dementia, and/or vascular dementia.

In one embodiment, methods and tools of this invention provide diagnostic and treatment for neurological conditions or neurological disorders such as Asperger's syndrome, Autism, Back Pain, Brain abscess, Brain damage, Brain injury, Brain tumor, Spinal tumor, Chronic pain, Chronic regional pain syndrome, Cumulative trauma disorders, Dementia, Epilepsy, Head injury, Headache, Motor skills disorder, Muscular dystrophy, Neurological manifestations of AIDS, Persistent Vegetative State, Restless legs syndrome or Spinal cord injury.

In one embodiment, methods and tools of this invention can be used in the diagnostics, treatment, and as part of a therapeutic or clinical approach for any neurological disorder, psychiatric disorder or related diseases and conditions.

In one embodiment, methods of this invention are used to stimulate cell cultures such as primary hippocampal, cortical, DRG culture or any other culture of connected neurons.

In one embodiment, this invention provides Axonal excitation. In one embodiment, this invention provides dendritic excitation. In one embodiment, this invention provides both axonal and dendritic excitations. In one embodiment, axonal or dendritic excitation or a combination thereof can be performed using electric stimulation.

In one embodiment, this invention provides rotating field stimulation in 1D culture. In one embodiment, this invention provides rotating field stimulation in 2D cultures. In one embodiment, this invention provides rotating field stimulation in humans. In one embodiment, this invention provides rotating field stimulation in animals. In one embodiment, this invention provides rotating field stimulation in rats.

In one embodiment, in parallel to pursuing dendritic excitation, axonal excitation can be considerably improved. In one embodiment, such excitation allows the targeting of a larger number of neurons for excitation, both in the culture dish and in the live brain. In one embodiment, such excitation has clinical applications.

In one embodiment, parameters such as fields and magnetic configuration used e.g. in the clover-leaf design in methods of this invention are chosen such that methods and devices of this invention can be clinically used. In one embodiment, methods and devices of this invention are used for treatment of human subjects.

In one embodiment, with a pulse that has a rise time that is about 1 millisecond, the dendritic response is greatly enhanced, and a change in electric potential can be created on the dendrites as well as on the axons.

The ability to stimulate 2D cultures magnetically is significant, particularly in view of the reported difficulty to achieve this using the standard single or figure-eight planar coil (Rotem, A. and Moses E. Magnetic Stimulation of One-Dimensional Neuronal Cultures, Biophys. J. 2008 June; 94(12):5065-78.). This ability may be a direct result of the rotation of the field, and it highlights two facts: 1) axons are the neuronal domain that is excited during TMS and 2) the axons have no preferred orientation in 2D cultures.

Surprisingly, 4 out of 15 cultures that could be excited by the crossed coil in one embodiment, were also excited by only a single coil of the pair. This is attributed to the fact that cultures that responded to the single coil had by chance several axons in the culture directed in the right orientation and could be excited by the induced electric field. Since the field of one coil is spatially directed, it is not surprising that the excitation of the cultures was directional-dependent and could be abolished by rotating the culture by 45° with respect to the coil.

The rotating field does more than just find the right orientation and excite the axons that lie in that direction. The probability that such an orientation exists, i.e. that several axons in the culture are oriented along a single axis, is presumably low. In all other cases the axon orientation is distributed randomly, and it is the scanning ability of the crossed coil that enables the excitation of those cultures.

One issue of obvious great interest is the application of the crossed coil geometry to human subjects. It is possible to manufacture large enough coils so that the human head can be positioned totally inside the crossed coils. The induced field will then rotate in space around the axis connecting the two poles of the system and is expected to be strongest just by the poles. A non rotating field similar in strength will also be induced along the circumference of each separate coil. As a consequence, this configuration will suffer the disadvantage of exciting many regions, both muscular and brain areas that are not targeted. A simulation demonstrating this is presented in the herein below.

A different kind of implementation of rfTMS to the human head is the cloverleaf design (see Methods and Materials), which achieves a focused scanning field capability while using the equivalent of the well-known figure-eight coil. This configuration is expected to be more agreeable for clinical use than the crossed coil one. The use of rfTMS on human subjects will eventually enable the excitation of currently inaccessible cortical regions, whose random axonal orientation is not amenable to excitation with a fixed-direction, non rotating field.

Another obvious advantage of rfTMS lies in eliminating the need for precise and maintained positioning and orientation of the coil, which is always time consuming and often necessitates cumbersome or expensive stereotactic equipment. There are of course advantages to the unique orientation of the induced electric field that the standard single or figure eight coils offer, for example the high specificity that can be achieved when the anatomy of the targeted region is known.

It should be emphasized that rfTMS as a technology is complementary in nature, and can be used in tandem with most other advances in the technology, e.g. deep TMS or novel repetitive frequency protocols. The additional power supply and the double magnets pose a minimal technical or financial burden, comparable to that incurred in a paired-pulse setup, whose advantages easily overcome the cost.

The sensitivity to field orientation has its origin in the directionality of axons, and in the fact that magnetic stimulation is achieved via axonal excitation. If the neuron could be excited at the dendrites then the dependence on field orientation would disappear (as in rfTMS) since the dendritic tree is isotropic. Because of their different physical properties, excitation of dendrites necessitates the application of pulses with longer duration, but these are currently accessible only using electric excitation as described herein below. Achieving long pulses in a magnetic stimulation is feasible, and is currently being pursued in our lab.

EXAMPLES

Example 1

Magnetic Stimulators for Rotating Fields

A rotating electric field was induced by using two independent sets of coils whose magnetic fields are perpendicular to each other and whose currents are phase shifted one from the other by a quarter of a cycle. Introducing a 90° phase lag between the two magnetic sinusoidal pulses, was achieved by precise triggering of two independent power supplies, each controlling a separate figure eight coil.

Power Supplies.

The two power supplies used were a Magstim Rapid TMS (Magstim, UK) and a home made stimulator (HMS). The HMS is based on a large 0.1 mF capacitor (Maxwell Laboratories, USA) with maximum voltage load of 22 kV and is able to obtain magnetic fields that are five times stronger than the field supplied at the sample by the commercially available Magstim Rapid. In order to achieve accurate phase lag between the two magnetic pulses, the two power supplies were synchronized using a signal generator (Keithley 3390 50 MHz Arbitrary Waveform/Function Generator, Keithley instruments, USA). The signal generator issued two trigger signals separated by ¼ of a cycle. This lag changed according to the coils used and ranged between 50-150 μs.

Magnetic Coils.

The magnetic coils were manufactured in the lab, using a polyester coated rectangular copper wire 0.01" thick and 0.25" wide (MWS Wire Industries, USA). Wires were turned around custom made frames. Wire turns were insulated with glass fibers and cast in epoxy (1 part Versamid 140 in 2 parts EPDN 814). For the crossed coils configuration (see below) 10 and 11 turns with inner diameters of 75 and 62 mm respectively were used. For the cloverleaf configuration (see below) an inner diameter of 20 mm was used. A pair of 25 turn coils was connected to the Magstim power supply and a pair of 30 turn coils was connected to the HMS.

Cloverleaf Coil.

Figure 3:
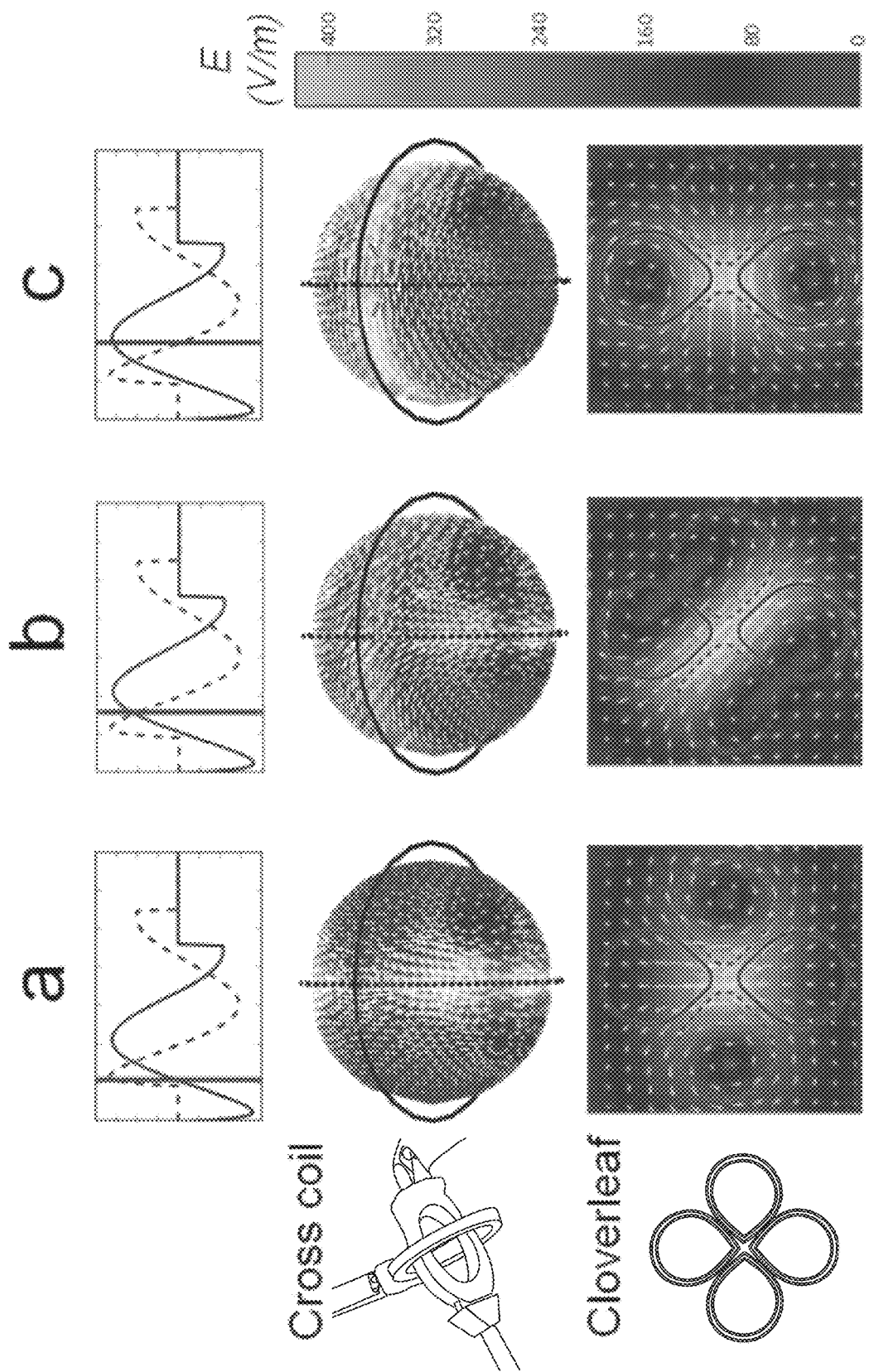
FIG. 3 illustrates embodiments of simulations of rotating induced electric fields. Upper row: idealized voltage traces—dashed line represents the voltage load on the dashed coils in the middle and bottom rows, solid line represents the voltage load on the solid coils. Solid vertical bars denote the time point for which the fields below were calculated. Middle row, cross-coil: two circular coils are connected to two independent current sources each producing a single sinusoidal pulse (as described in the top row). The resulting electric field on the surface of a sphere positioned inside the coils is simulated (magnitude according to color code, direction by white arrows). a) After the horizontal coil completes ¼ of a cycle, the vertical coil commences its pulse and dominates the induction; b) A quarter of a cycle later, both coils induce an equal field and the effective field is diagonal. c) After another ¼ of a cycle, the horizontal coil completely takes over and the resulting field is rotated by 90° with respect to the original orientation in a). The point of rotating field ("hot spot") is located on the sphere surface at the crossing point of the two coils (dashed ellipse). For details of the simulation see herein below. Bottom row, cloverleaf coil: 2 pairs of modified figure eight coils are connected to two independent current sources each producing a single sinusoidal pulse (the voltage load on the coils is described in the top row). The resulting electric field 3 cm above the coil is simulated (magnitude according to color code, direction by white arrows). a) After the solid pair completes ¼ of a cycle, the dashed pair commences its pulse and dominates the induction, resulting in a vertical field. b)¼ of a cycle later, both coils induce an equal field and the effective field is diagonal. c) After another ¼ of a cycle, the solid pair completely takes over and the resulting field is horizontal. During a full cycle the orientation of the induced field rotates, sweeping 270°, while the maximal excitation remains in the center of the cloverleaf ("hot spot"). For details of the simulation see the Supplementary Material.

One such possible configuration, shown in FIG. 3, employs two standard figure eight coils. The induced electric field just above the center of each figure eight coil is directed perpendicular to the axis connecting the two coil centers so that the two figure eight coils create fields that are perpendicular to each other. Discharging both figure eight coils together will cause a resultant vector which is the sum of the two fields. Discharging the second figure eight coil one quarter of a cycle after the onset of the first one, results in a rotating electric field at the center of the system. Introducing a 90° phase lag between the two magnetic sinusoidal pulses, is achieved by precise triggering of two independent power supplies, each controlling a separate figure eight coil.

Crossed Coils.

A second configuration is shown in FIG. 3, and involves two coils whose planes are perpendicular. Close to the poles, where the two coils intersect, the electric field is large and directed tangentially in the plane of the coil. As in the cloverleaf design, each of the coils is connected to a separate power supply and one of the magnetic sinusoidal pulses is phase shifted by 90° with respect to the other. For the crossed coils (see FIG. 1) two circular coils were used with 10 and 11 turns and inner diameters of 75 and 62 mm respectively. The two coils were positioned one inside the other, while keeping their planes perpendicular. The hotspot of the crossed coil is located near the poles of the construct, where the two coils intersect (FIG. 1$d$-$f$) and the induced fields of the coils are perpendicular to each other. This configuration is simpler than the cloverleaf coil (see below), and does not suffer from mutual induction losses, since the planes of the two coils are perpendicular.

Measurement of Induced Electric Field and Calibration of the Coils

To measure the induced electric field of the coils, a pick up coil 40 mm in diameter was used. The pick-up coil was positioned inside the measured coil, parallel to its plane. The measurements were not sensitive to whether or not the pick-up coil was concentric with the magnetic coil. The pick-up coil was used to calibrate the cross coil as follows: first, the relation between the power setting of the stimulator and the resulting induced field of each the coils was measured and a linear relation was found for each pair of stimulator and circular coil. Second, the proportionality constant of the HMS coil vs. the Magstim coil was compared and it was found that the induced field at 100% power setting of the Magstim is equivalent to 3 kV setting of the HMS. This determines the maximum intensity of a rotating field pulse, which for the crossed coil was equal to 345±25 V/m at the hotspot of the coverslip plane. This equivalence was used during our experiment, keeping the ratio of 3 kV/100% for any setting of pulse intensity. For example, when delivering a pulse that is half the maximum intensity, 50% Magstim power and 1.5 kV HMS load were used while for a pulse that is ¾ of the maximum intensity 75% Magstim power and & 2.25 kV HMS load were used.

Estimation of Induced Electric Field at the Hotspot.

To estimate the induced electric field at the location of nerve cells, the dimensions of conducting medium located inside the coil was considered. Since any induced electric field outside the conducting media is cancelled at the interface by surface charges, the relevant length scale for calculating the electric field resulting from a uniform magnetic field is that of the cross section of conducting media parallel to the plane of the coil. In the case of the 2D culture stimulation, this was taken as the dimension of the sphere ball (5 cm in diameter, due to the flattened base of the sphere, and residue of air in the upper part of the sphere). In the case of TMS on rats, this was taken as the ear to ear distance of each rat (between 3-4 cm in diameter).

Simulating the Induced Electric Field for the Cloverleaf Coil Configuration

Calculating the Induced Electric Field for Simulations

The electric field, produced by the cloverleaf coil, was calculated by numerical calculation. To this end, the shape of the coil windings was described by third order polynomial splines in x and y and then discretized to straight segment vectors $l_i$ of 1 millimeter length. To account for the height of the wire, 6 instances of the coil, each shifted by 1 mm in z were considered, each conducting ⅙ of the total current. Each of the segments contributed to the magnetic vector potential A according to:

$$A(r,t) = \frac{\mu_0}{4\pi} I(t) \sum_{segments\, i} \frac{l_i}{|r_i - r|},$$

where $r_i$ is the vector pointing to the center of the segment i. Once the vector potential is calculated, the induced electric field is $$E(r,t) = -\frac{\partial A(r,t)}{\partial t}.$$

The precision of the numerical calculation was tested for idealized circular coils by comparison with the analytical solution [3]. The discretization in 1 millimeter segments was sufficient to reproduce the analytical solution with less than 0.01% error in electric field intensity, assessed 1 cm from the coil surface. Simulations using spiral-like windings were also compared, as they appear in reality to simulations in which inner windings were scaled copies of the outmost winding. The only difference appeared at he begin and end of each winding. As begin and end of the clover-leaf coil wires are located away from the center of the coil, the small deviations are not relevant for the simulations and scaling was used to reproduce the shape of the inner loops (see also FIG. 13).

Threshold for Neuronal Excitation

To judge the stimulation efficiency of the clover-leaf coil the expected excitation threshold for various orientations between coil and neurite were estimated. Using the electric field E induced by the clover-leaf coil 3 cm above its center, the effect of the on the membrane potential V of a passive cable (1 µm diameter, 1 mm length) was calculated as described earlier (Rotem and Moses 2008), using the cable equation with a source term accounting for the field E:

$$\lambda^2 \frac{\partial^2 V}{\partial l^2} - \tau \frac{\partial V}{\partial t} - V = \lambda^2 \frac{\partial E_l}{\partial l}.$$

The axial length constant $\lambda=384$ µm and the time constant $\tau=300$ µs were chosen to approximate the conditions of an unmyelinated axon (Rotem and Moses, 2008), the l-axis runs parallel to the cable and $E_l$ is the projection of E onto this direction. The cable ends are assumed to be sealed, implying the boundary conditions:

$$\frac{\partial V(0,t)}{\partial l} = \frac{\partial V(L,t)}{\partial l} = 0.$$

Using the axial resistance $r_i$ the source term is equivalent to a current injection $$I_i = \frac{1}{r_i} \frac{\partial E_l}{\partial l}$$

with opposite signs at the two ends. To perform the simulation, the IClamp method of the simulation environment NEURON was used. For each angle between x-axis and neurite the induced field was calculated for a certain maximal coil current and hence a certain maximal amplitude of the x- and y-components of E ($E_x^{max}$ and $E_y^{max}$). Next, the projection $E_l$ was used to calculate the resulting time course of the membrane potential. The calculation was repeated varying $E_x^{max}$ and $E_y^{max}$ in a binary search, to find the value at which the membrane was depolarized by just 30 mV, our criterium for successful excitation. The systematic variation of the angle and coil current as well as the communication of the respective current injection $I_i$ to NEURON were automated using Python.

Rotating Magnetic Field Measurements

The electric field was measured using a circular positioned in plane of the crossed coils. The measurement was carried out both for the assembled cross coil, with the probe rotated by 90 degrees between measurements, and for each of the coils separately. The resulting fields are shown in FIG. 1, where the phase shift is obvious, and the resultant sum of the two vectors is shown as well. The total resulting electric field performs a rotation, scanning approximately 270° in the three quarters of a cycle, which is on the order of 300 µs. Its magnitude, depicted by the radius of the vector rotating in FIG. 1e, is kept practically constant during the first quarter of rotation, at a value comparable to the peak strength obtained with a single coil, on the order of 300V/m.

Excitation of 2D Neuronal Cultures

Figures 8, 9:
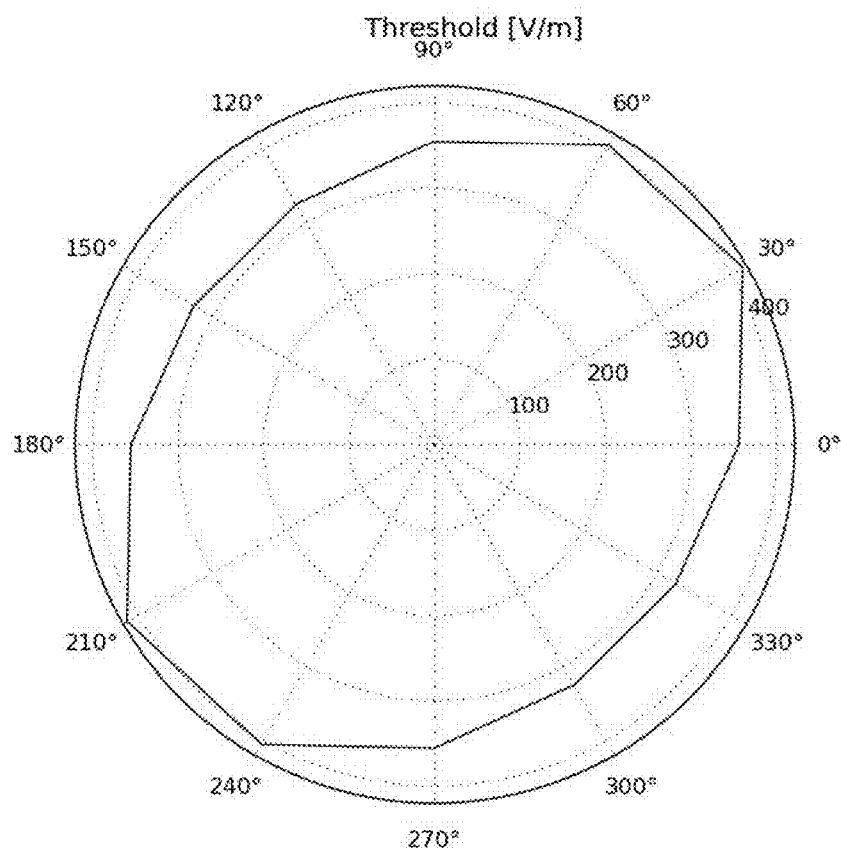
FIG. 8 is a summary of magnetic stimulation response in both neuronal 2D cultures and anesthetized rats.
FIG. 9 demonstrates an embodiment of orientation dependence; The cloverleaf coil alleviates the orientation dependence of magnetic stimulation: The calculated electric field, induced by the cloverleaf coil (FIG. 3) was used to simulate action potential generation in an axon with 1 μm diameter and 1 mm length containing voltage sensitive sodium, potassium and leak conductances (see Material and Methods). To characterize the threshold at different orientations of the axon with respect to the coil, the amplitude of the current pulse was increased until the magnetic stimulus triggered an action potential. The maximal amplitude of the electric field that was induced at this current amplitude by each of the coils is plotted here against the angle between the axon and the x-axis. The simulation predicts that the threshold of action potential generation by magnetic stimulation is only weakly dependent on coil orientation, if a cloverleaf coil is used.

The main result of using the crossed coils can immediately be seen by looking at two dimensional (2D) cultures. While previously the excitation of 2D cultures with magnetic pulses was unsuccessful, in the crossed coils this was easily achieved. As shown in FIG. 8, half of the 2D cultures tested (15 out of N=30) were excited by the magnetic stimulation. Surprisingly, with this geometry approximately 25% (N=4) of the 2D cultures that responded to the crossed coils also responded to excitation when using only a single coil of the cross coil system, with a threshold field that was either similar or 15% stronger than that of the cross coil. The estimated electric field threshold for excitation was distributed around a mean of 360±40 (SD) V/m and agreed with that reported previously for 1D cultures (300±130 (SD) V/m).

A test for the directionality is found in two cultures that were excited both by a single coil and the cross coil. By physically rotating the culture 45° with respect to the coil it could be tested whether the initial random orientation was dominant in enabling the excitation. The single coil stimulation was indeed sensitive to this rotation, with the threshold climbing beyond the maximum field strength of our system. Strikingly, stimulation with the cross coil showed no sensitivity to the rotation, and the culture responded at all angles.

Preparation of Primary Culture.

To test the effect of the new stimulators, the stimulators were first applied on two-dimensional cultures. All procedures were approved by the Weizmann Ethics Committee (IACUC). The cultures were prepared from dissociated hippocampus of prenatal rats following a previous protocol (M. Papa, M. C. Bundman, V. Greenberger, M. Segal, J Neurosci 15, 1 (January, 1995)). Cells were plated on 30 mm #0 glass coverslips (Menzel-Glaser, Germany), at a density of 3 million cells per coverslip.

Trans-Vessel Magnetic Stimulation (TvMS) of Primary Culture.

To measure the response of cultures to magnetic stimulation, the cultures were stained in calcium sensitive fluorescent dye and calcium transients were imaged (A. Rotem, E. Moses, Biophys J. 94, 5065 (June, 2008) fully incorporated herein by reference) while magnetic pulses were applied on the cultures. The positioning of the coils with respect to the culture differed between the two sets of coils.

In the case of the crossed coils (FIG. 1c), the culture was placed in a near-spherical glass ball, approximately 60 mm in diameter, whose bottom was flattened to create a circular base approximately 30 mm in diameter on which the coverslip lay. At the top of the sphere a slot was opened through which the coverslip could be inserted and at the base of the sphere a viewing hole 13 mm in diameter was made near the circumference of the base, covered with an optically transparent glass coverslip. The glass sphere was placed inside the crossed coils, with the flattened base positioned over one of the poles (see FIG. 1c) and an inverted microscope positioned under the viewing hole.

In the case of the cloverleaf coil, the culture was positioned 5 mm below the center of the to coil and parallel to its plane. An inverted microscope was positioned below the culture.

Transcranial Magnetic stimulation of anesthetized rats.

To further assess the excitation power of the new magnetic stimulators their effect on adult rats anesthetized with ketamine and xylazine was tested. Ketamine in combination with xylazine has been shown in rats to result in sufficient anesthesia and analgesia without depressing vital functions (for reference see S. Zandieh, R. Hopf, H. Redl, M. G. Schlag, Spinal Cord 41, 16 (January, 2003). All procedures were approved by the Weizmann Ethics Committee (IACUC). Prior to the experiments rats were anesthetized using 75 mg/kg Ketamine (Kepro, Holland) and 7.5 mg/kg Xylazine (Kepro, Holland) injected IP. Rats were anaesthetized approximately 1 hr prior to the beginning of the experiment and hence after, Ketamine was injected IP throughout the experiment at an average rate of 75 mg/kg/hr according to the animal's level of anesthesia. At the end of the experiment, the rats were euthanized using 150 mg/kg of Pentobarbitone Sodium (CTS, Israel).

During the TMS protocols, rats were positioned so their motor cortex is at the focus of stimulation: In the case of the crossed coils, the rats head was placed inside the two coils, with the motor cortex located just below one of the poles. In the case of the cloverleaf coil, the center of the coil was placed just above the motor cortex.

To monitor the effect of TMS on the rat, evoked muscle potentials were recorded from its hind legs using an EMG system. The stimulation threshold, i.e. the minimal magnetic field required to create a response as recorded in the EMG was measured.

Excitation of Rat Motor Cortex

The cross coil configuration is particularly well suited for application on rats, since the head of the animal fits well inside the cross coil, with the cortex placed on the joint axis of the two coils (their shared diameter, see FIG. 1f), where the field is maximal. 9 animals were tested for the response of the Gastrocnemius muscle to magnetic stimulation, as measured by an Electromyogram (EMG) electrode on the leg of the animal. The major difficulty in this test is to differentiate between the excitation of the motor cortex and that of the spinal cord. This was done using the different latencies of the response in the two excitation modes.

Figure 2:
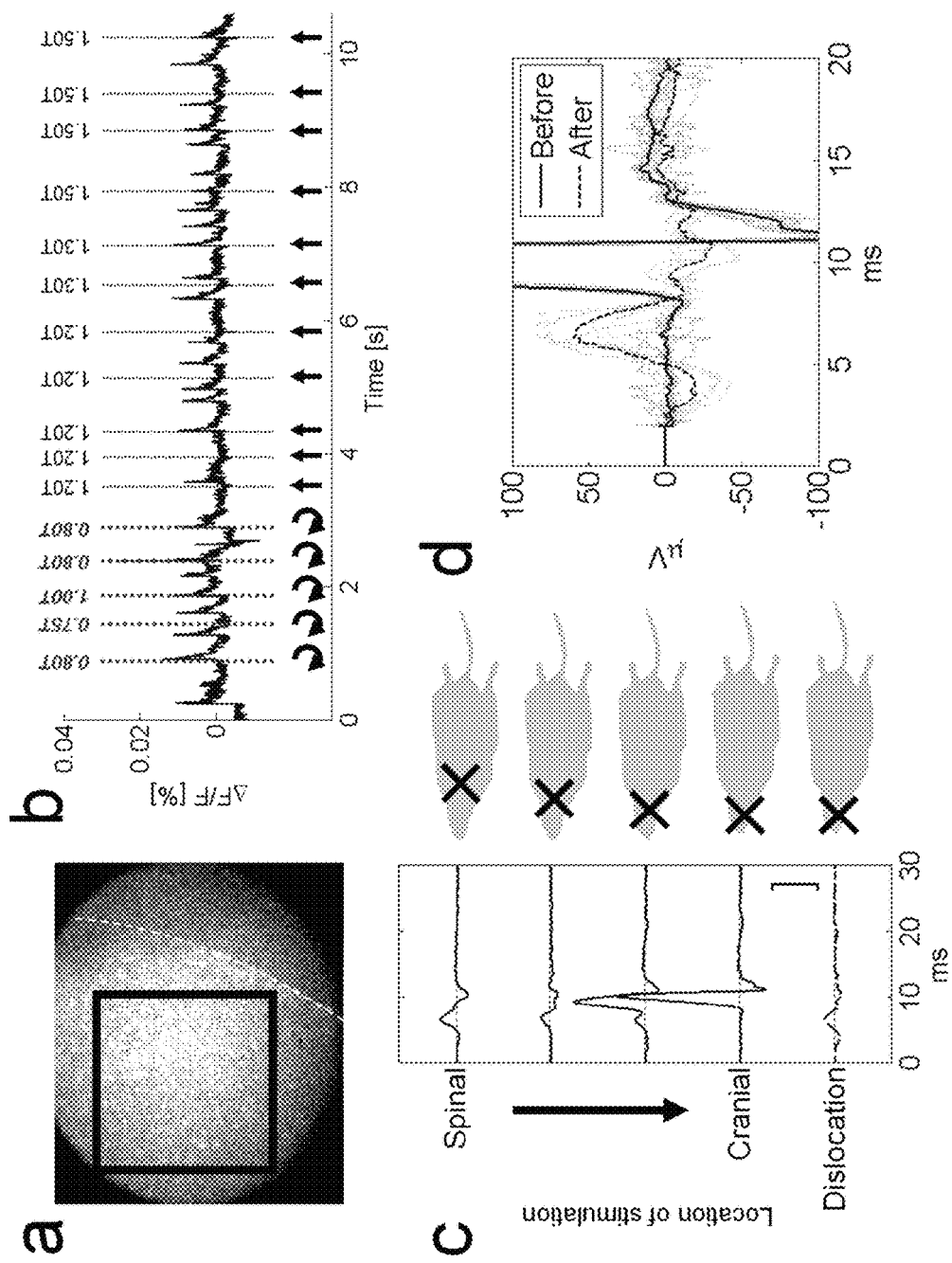
FIG. 2 demonstrates embodiments of response to stimulation; a) the response of 2D Neuronal culture to rfTMS. The culture activity was imaged through the viewing hole (see FIG. 1b). The black box indicates the region of interest on which the signal was averaged. The dashed white line indicates the borders of the coverslip on which the culture was grown; b) The calcium dependent fluorescence of the region of interest in a). Dashed lines are events of magnetic stimulation using the cross-coils while black are when using only one of the coils. The intensity of each stimulation is noted in Tesla. Note that activity is induced by the cross-coils already with 0.8 T, while a single coil will only induce activity at around 1.5 T; c) The response of rat motor cortex to rfTMS. Graphs of EMG recording of the Gastrocnemius when using the cross-coils to stimulate a rat in different locations. Each location is illustrated to the right of the response trace with the black cross representing the cross-coil. The last row was performed after cervical dislocation of the rat. Scale bar is 200 µv; d) A comparison between the last two rows in c). The solid line is the average response of the rat to rfTMS over its head before dislocation and the dashed curve is the average response of the rat after dislocation.

As shown in FIG. 2d, the response of the Gastrocnemius to stimulation was complex yet reproducible. Two typical latency times were observed, which were associated with the spinal response (3.2±0.2 ms (SE)) and with the cortical response (7.4±0.4 ms (SE)). In most cases, the spinal and cortical responses could be differentiated reliably by the latency time. Cervical dislocation or sectioning of the spine abolished the longer latency response, while leaving the shorter one active for several minutes. The spinal response was typically excited at a lower magnetic stimulation threshold than the cortical one.

In eight of the nine animals tested, a clear response of the motor cortex to cross coil stimulation was observed. Four of these animals also responded to stimulation using only a single coil of the cross coil system. As in the neuronal culture stimulations, when using only a single coil the electric field threshold was always equal to or higher than that of the double coil system (between 0% and 33% higher, 10% on average). The estimated electric field threshold for excitation was distributed around a mean of 250±10 (SD) Vim.

The dependence of cortical responses on orientation was assessed using the cross coil. With the rotating field, no dependence was observed and the same response was measured at all relative orientations between the coil and the animal, so that positioning of the rat was not a critical parameter of the experiment. In contrast, using a single coil necessitated a precise position of the rat head inside the coil to assure the effective stimulation of the cortical response. On the other hand, there was no discernible difference in the threshold needed for cortical excitation with a single coil or with the cross coil, once the optimal orientation for single coil excitation was determined. Several attempts were made to stimulate the cortex with a simple circular coil as described herein below but no clear excitation was achieved.

A 50% increase in excitation thresholds was observed immediately after Xylazine anesthesia injections, which decreased back to baseline values after 1 hr. Ketamine anesthesia injections did not affect the measured thresholds (more details can be found herein below).

Electric Stimulation of One-Dimensional Primary Culture.

To compare the response of cultures to different durations of stimulation, one-dimensional cultures were stimulated electrically. These cultures were patterned into straight lines 200 μm thick and 8 mm long on 13 mm glass coverslips using a protocol developed in the lab. Details can be found in O. Feinerman, E. Moses, J Neurosci Methods 127, 75 (Jul. 15, 2003) fully incorporated herein by reference. Stimulation was achieved using bath electrodes made of 2 parallel platinum wires (0.005" thick, A-M Systems USA) 2 cm long and 3 cm apart that were immersed in the recording dish. For stimulation, a bi-polar square pulse was used, lasting between 0.1-10 ms with amplitudes of 1-36V peak to peak.

Results

Measurements of Rotating Field Stimulations

FIG. 1e shows the resulting electric field of a prototype crossed coil, which scans almost all directions.

Electric Stimulation of One-Dimensional Culture.

Figure 14:
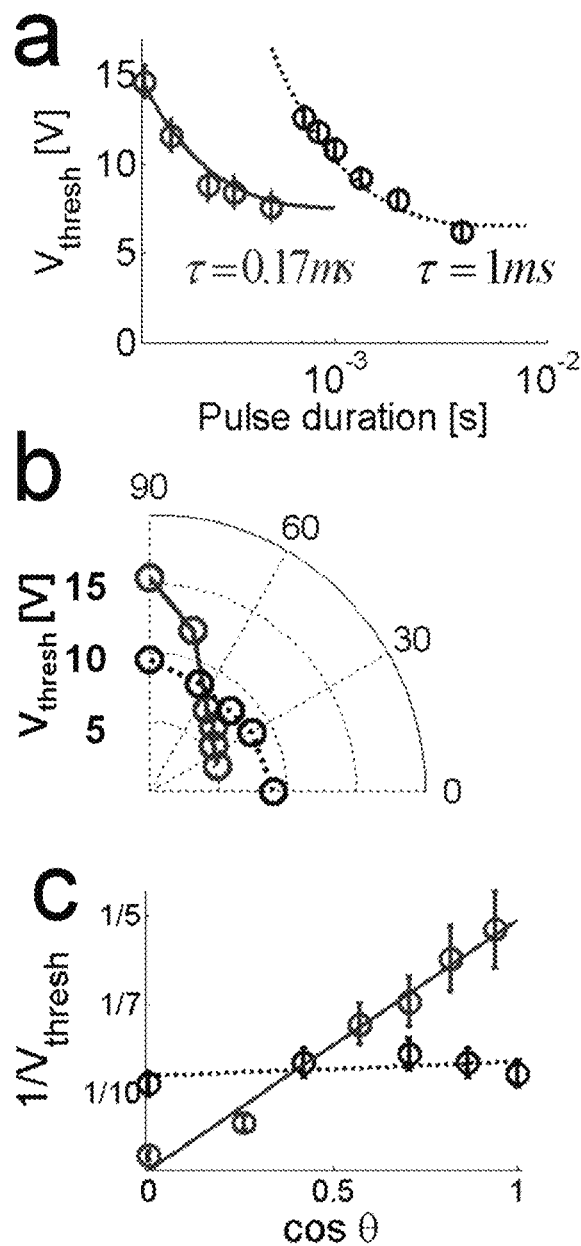
FIG. 14 shows responses of one-dimensional cultures to electric stimulation with varying orientation and pulse duration. a) The solid culture responded to brief stimulations (~0.1 ms), while the dashed responded only to stimulation longer than 1 ms. The threshold decreases with pulse duration, then reaches a low saturated steady state (not shown). b) Response of the cultures to rotation of the field direction with respect to the culture orientation. The dashed culture has a constant response at all angles, while the solid culture (at short pulse durations) is much easier to excite when the electric field is at 0 degrees, meaning parallel to the orientation of the culture. c) Angular dependence of threshold shown in (b), as a function of the cosine of the angle. For the solid culture a linear relation is clear, indicating that it is indeed the axonal projection on the direction of the field that determines the threshold for excitation. The dashed culture is insensitive to the orientation of the electric field.

The principles behind the idea of axonal versus dendritic excitation can be tested using direct bath electrode stimulation, since the length of the electric pulse can be easily controlled (in contrast to the magnetic pulse). The duration of current injection by the electrodes can easily be varied from 100 μsec to 10 ms. FIG. 16 shows two examples of cultures. As shown in FIG. 16a the first is excited already with the 100 μsec pulse, indicating that there are enough axons in the culture that are parallel to the electric field between the electrodes, and they excite the rest of the network. The second example is a culture that does not respond at 100 μsec, but needs a pulse of a few ms to respond. Here only dendritic excitation is expected to be in effect. Indeed, as predicted, FIG. 14b shows that the first culture is highly dependent on orientation, and the amplitude needed for excitation when the field is parallel to the culture (and to the axons) is much lower than that needed for excitation when the field is at an angle to the axons. On the other hand, the culture that responds by dendritic excitation has no observable dependence on the orientation of the culture with respect to the electric field. This result considerably strengthens the understanding that the two modes of excitation—dendritic versus axonal—can play a very different and crucial role in initiation of activity in the culture.

Magnetic Stimulation of Primary Culture.

27 cultures of two-dimensional hippocampal neurons plated on 30 mm diameter glass coverslips were tested. Out of these, 13 were stimulated using a circular coil positioned horizontally above the culture, 10 were stimulated using the crossed coil configuration (see methods), and 4 were stimulated using both methods. Of the 14 cultures that were stimulated using the crossed coils, 5 responded to the rotating field and just one responded also to a single vertical coil of the crossed system (FIG. 4). Of the 17 cultures that were stimulated using a horizontal coil just 3 responded. All 4 cultures that were stimulated with both methods responded to the rotating field while only one of these cultures responded to the horizontal coil. The stimulating threshold in both methods was similar, with an average of 460±40 V/m. This threshold is ~50% higher than the threshold measured for one-dimensional cultures while the success rate of the crossed coil (36%) is ~50% lower than that of one dimensional cultures [Rotem & Moses Biophys J. 2008]. The results are summarized in FIG. 8.

Example 2

Electric Vs. Magnetic Excitation of Neuronal Cultures

According to this aspect and in one embodiment, electric stimulation is tested for insight into magnetic stimulation. Because long pulses (~1 ms) are easy to excite electrically but not magnetically, and since the fundamental mechanisms behind the two modes of simulation are similar, the response of cultures to varying duration of electric pulses was investigated. Based on this, reasonable conclusions and conjectures were made on the mechanism underlying magnetic stimulation.

To demonstrate the time dependence, cultures that can be stimulated both electrically and magnetically were tested, and compared to those that can be excited only electrically. It naturally turns out that cultures that respond to the magnet respond to short electric pulses. What is not obvious is that cultures that do not respond to magnetic stimulation also do not respond to short pulses, and can be excited only with long electric pulses.

Methods:

Electric Stimulator

The neuronal culture, which is grown on a circular coverslip, was placed at the center of a recording dish as described herein above. A custom made annular Teflon frame fit into the sample dish and could rotate freely above the culture. Two parallel platinum wires (0.005" (0.127 mm) thick, A-M Systems USA) 20 mm long and 12.5 mm apart were mounted along the bottom of the frame about 1 mm above the culture and immersed in the recording medium.

The wires were connected to a custom made battery powered stimulator triggered via a photo-coupler to isolate the sample from any electrical noise originating in the power grid. For stimulation, a bi-polar square pulse was used, with a variable duration lasting between 0.01-10 ms and with amplitudes of 1-36V peak to peak. The trigger and pulse duration was precisely controlled by a signal generator (DS345 Synthesized Function Generator Stanford Research Systems Sunnyvale, Calif., USA).

Neuronal Cultures

A variety of experimental protocols were used to obtain cultures for different aspects of the experiment. Both two dimensional (N=15) and patterned one-dimensional (N=98) geometries of cultures were used. Neurons from rat hippocampus and cortex and from mouse dorsal root ganglion were taken. All these types were used to compare the electric vs. magnetic excitability of cultures. Rat hippocampal cultures patterned into straight lines that were 200 μm thick and 8 mm long on 13 mm glass coverslips, grown according to the protocol developed in our lab. (Feinerman O, Segal M, Moses E. Signal Propagation along Uni-dimensional Neuronal Networks. J. Neurophysiol. 94: 3406-3416, 2005).

Measurements

To compare between the two types of stimulations, the minimal electric pulse duration required for stimulating the culture was measured and termed the pulse duration threshold (DT). The DT was determined by setting the stimulator current at its maximal amplitude and tuning only the duration of the bipolar pulse using a binary search algorithm until a threshold is determined.

Figure 10:
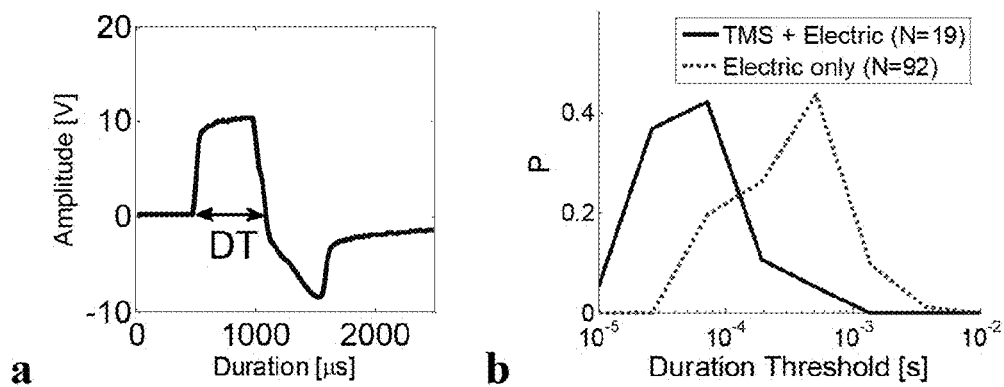
FIG. 10 illustrates an embodiment of electric stimulation of neuronal cultures. a) A typical voltage trace of the electric pulse used to stimulate cultures. Pulse duration (DT) could be varied continuously between 10 μs and 10 ms. b) A semilog histogram of the pulse Duration Threshold, the minimum pulse duration required for stimulating a culture. Cultures that were excitable both magnetically and electrically are displayed in a solid curve. Cultures that could only be excited using an electric pulse are displayed in a dashed curve.
Figure 11:
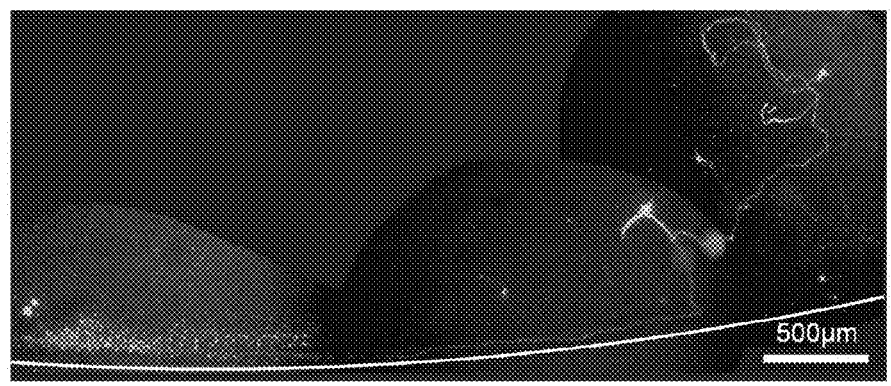
FIG. 11 is a fluorescent image of a GFP expressing neuron grown in culture. The culture was plated on a 30 mm coverslip (the white arc in the figure runs on the coverslip rim). The neuron's axon can be tracked as it follows the coverslip circumference tangentically along 3 mm.
Figure 12:
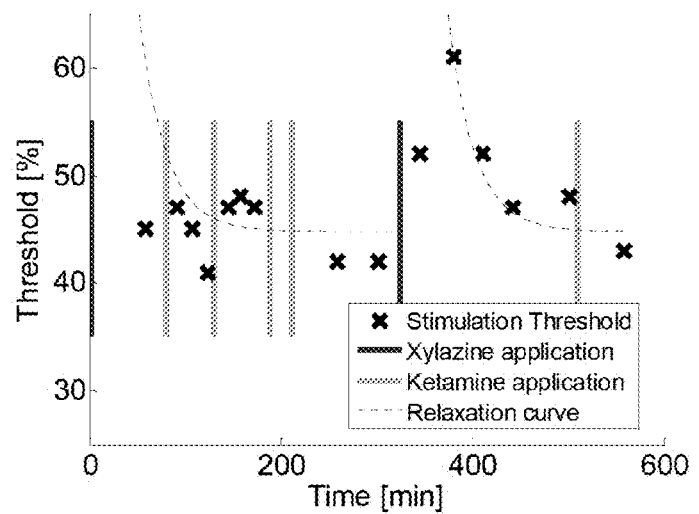
FIG. 12 demonstrates effects of anesthesia on stimulation threshold. The magnetic threshold for spinal stimulation of a rat was measured 15 times along a time course of 10 hours (black crosses). A solution of Xylazine and Ketamine was administered twice during the experiment (first and sixth vertical lines) and a solution containing only Ketamine was administered in five additional times (remaining vertical lines). A relaxation curve was fitted to the data, assuming that the anesthetic effect of Xylzine gradually rises to a peak after the injection and then exponentially relaxes back to the baseline measurements.

Results: N=112 cultures were tested for both magnetic and electric excitability. All cultures responded to electrical stimulation, while only 16% (N=19) responded to magnetic stimulation. The distribution of all DTs is described in FIG. 10. The DT of the magnetically excitable cultures had a mean of 110±40 μs (SE) while the average DT of all cultures that did not respond to magnetic stimulation was 510±50 μs (SE).

The Equivalence of Induced and Conductive Electric Fields

The passive cable equation that describes the response of neurites to external electric field does not depend on the source of the field. The electric field induced by the TMS pulses is similar in strength to that produced by the bath electrodes. In principle, the overall geometry of the fields and the motion of counter ions can be different depending on the precise coil configuration, and the boundary conditions may differ. However, at the scale of an axon that is oriented in the direction of the field, the fields can be assumed to be practically identical.

Comparing the effective pulse width of an electric and magnetic pulse warrants some care. As shown in FIG. 1d of the manuscript, the typical magnetic sinusoidal pulse of 240 µs induces a cosine for the electric field, and has three stages, positive for about 60 µs, negative for 120 µs and ends with another positive stage of 60 µs. The corresponding changes in membrane potential are also bi-polar, and bring a shift in the potential that is maximally positive at a phase of $\pi/2$ and maximally negative at $3\pi/2$. In comparison, FIG. 10a shows the basic bi-polar square electric pulse which has two stages, first the positive stage and then the negative. The corresponding membrane potential of a typical axonal or dendritic ending or curve is uni-polar. The potential rises to a value similar to that in the corresponding magnetic pulse, but does not shift to the opposite sign after relaxing to zero.

In principle, whether the neuron undergoes a negative or positive potential change should make a difference in the response of the neuron, with a higher probability for the positive potential shift to create an action potential. However, no obvious dependence on the order of the polarity was found, indicating that, for a given direction, axons and dendrites were as likely to point in both opposite orientations.

The use of an electric pulse shaped like the magnetically induced one was tested as well, with a quarter cycle in the plus direction, then two quarters in the opposite, negative direction and ending with the final quarter positive again. The results were similar to ones with the original pulse used. It has been seen that all cultures that respond to pulse durations shorter than 60 µs were also excited by TMS, and perhaps more significant, only those. This is in good agreement with the pulse duration of TMS, which is 60 µs.

Longer Pulses Excite More Cultures

From the distribution of DTs (FIG. 10b) it can be concluded that longer pulses are more efficient in exciting cultures. This, together with the equivalence between magnetic and electric stimulation implies that longer TMS pulses will be more efficient in exciting neurons, with a critical timescale of 200 µs. For example, a TMS pulse that will last 500 µs is expected to excite 80% of all cultures.

Using the Conventional Circular Coil

Results in Culture Experiments

In a previous study, randomly connected two-dimensional (2D) cultures could not be magnetically stimulated using standard circular coils, even at high (~5 T) magnetic fields produced by the homemade power supply ([Rotem & Moses BioPhys J 2008]). This study was based upon examination of 11 cultures. In the current study, two out of 12 cultures that responded to the crossed coils were also responsive to the standard coil (another 3 cultures were responsive to the standard coil and were not tested using the double coil due to deterioration of the sample over time).

A possible explanation for this phenomenon is that in these cultures a subset of the axons is oriented in a direction parallel to the induced electric field. Since the electric field lies on rings concentric with the cover glass boundaries, axons that might lie in this direction were searched. An example of one such GFP stained neuron is presented in FIG. 17. The axon of this neuron extends to 3 mm and grows parallel to the cover slip boundaries. The orienting effect of boundaries on axons has been previously demonstrated (Fienerman et al. J. Neurophys 2005). If indeed the boundary forces a large number of neurons to have axons oriented along the rim surrounding the culture then these would be excited by the induced electric field and could initiate activity in the whole culture.

Results in Rat Experiments

In addition to the successful crossed coil excitation of cortical activity in rats, as reported herein above, rats were magnetically stimulated using the standard single circular coil. While cervical excitation was evident, a cortical component in the signal could not be differentiated. Therefore the circular was mostly used for the task of characterizing the effect of the anesthetic agents Ketamine and Xylazine on the threshold for excitation of the cervical activity. One experiment using the crossed coils was conducted to verify these results.

Effect of Anesthesia on Stimulation Threshold

In the experiment described in FIG. 17 a series of 15 threshold measurements were performed while the animal was anesthetized and given several doses of anesthetics, using either a combination of Ketamine and Xylazine or Ketamine alone. As seen in the Figure, the threshold measured after doses of Ketamine alone differed by no more than 10% from each other, while Xylazine increased the threshold by about 50%. Since the accuracy in determining the threshold is on the order of 10%, it can be concluded that electric field thresholds should not be measured in proximity to Xylazine application (relaxation times were derived from the fit of the data to be approximately 1 hour), but that Ketamine application does not affect the threshold by more than the typical statistical deviation of the measurements.

The Cloverleaf Design

The crossed coil configuration is radically different from standard coils that are currently in clinical use. This configuration was found to be highly efficient on cultures and rats, but some complications may arise when applying it on humans. In particular, the large structure and positioning of the head inside the cage-looking setup could discourage subjects and interfere with the patient peace of mind during the experiment. In addition, the fields induced by the crossed coils reach much deeper areas in the brain than standard coils and may activate untargeted regions or muscles during the experiment.

Figure 13:
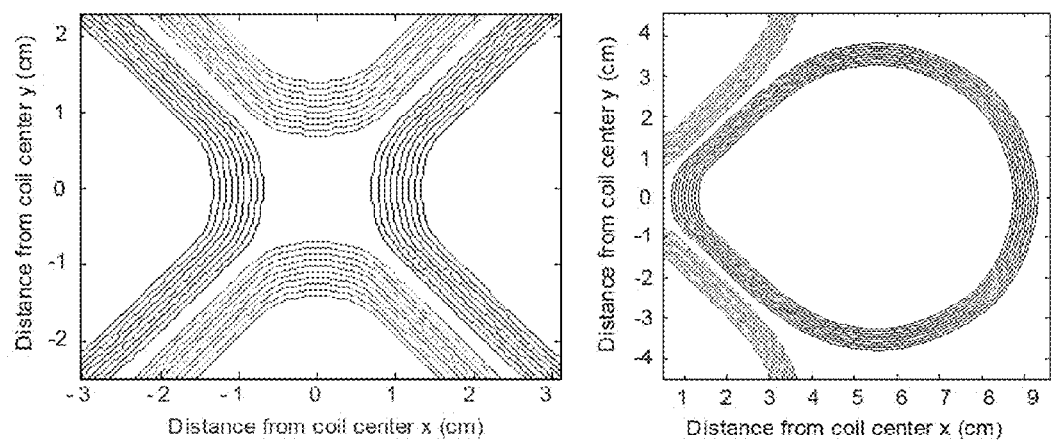
FIG. 13—Reconstruction of the dense cloverleaf coil. Left: Zoomed in view of the coil center. Lines represent the wires of each coil loop. The 10 top and bottom v shaped lines correspond to the vertical leaves and the 9 left and right v shaped lines the horizontal leaves. Right: Closed circular lines represent the overall view of one of the coil leafs. The coil is not spiraled. Each inner loop is a scaled copy of the external loop.

As an alternative, an embodiment a cloverleaf configuration is described herein. The cloverleaf configuration is similar to currently available conventional products. The cloverleaf consists of two pairs of "figure of eight" coils (FIG. 13). Each pair is connected to an independent power source. The two pairs are positioned on the same plane and perpendicular to each other so that at the hotspot, their resulting electric fields are perpendicular. Similarly to the crossed coil setup, the pulses of the pairs are separated by a phase of 90 degrees. The resulting electric field at the hotspot completes ¾ of a circle during one combined pulse. The rest of the characteristics of the electric field, in terms of strength, focus and decay on the Z-axis are similar to that of the conventional figure of eight coils.

An advanced version of the cloverleaf coil is the dense cloverleaf (FIG. 13). In this coil, each circular component was distorted near the hotspot to minimize the empty gap above the hotspot, thus increasing the field strength at the hotspot itself while decreasing the volume of the hotspot.

Example 3

Magnetic Stimulator for Dendritic Excitation

Figure 7:
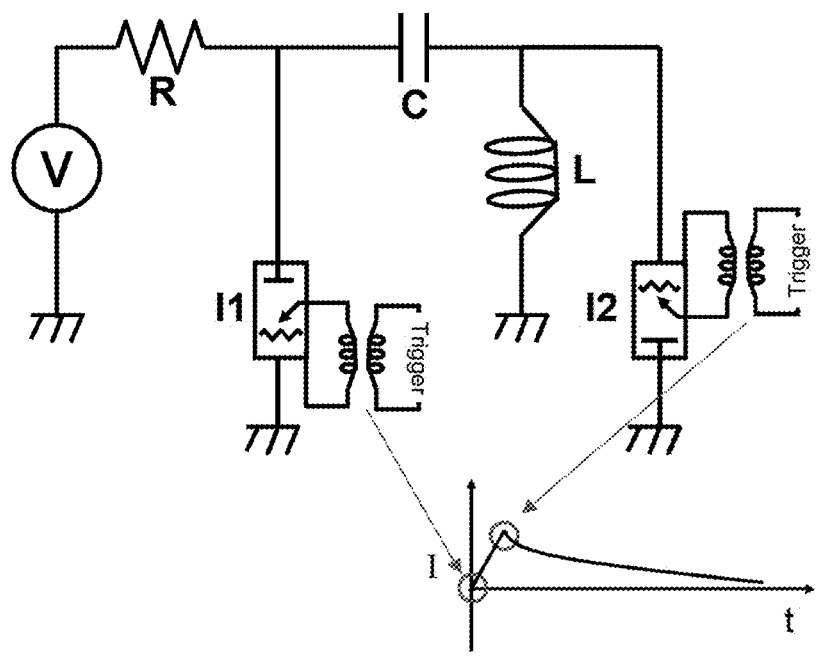
FIG. 7 illustrates an embodiment of a larger stimulator with a capacitor C of 4.8 mF and a maximum voltage load of 6.5 kV capable of delivering about 10 T with a rise time of 1 ms. Ignitron I1 was used to initiate discharge through the coil and Ignitron I2 was used to shortcut the coil and stop the discharge through the coil.

In one embodiment, dendritic excitation requires magnetic pulses with a rise time of 1 ms, made possible by increasing the capacitance of the stimulator. For this a larger stimulator was constructed with a capacitor C of 4.8 mF and a maximum voltage load of 6.5 kV (3650CMF3480, General Atomics Electronic Systems, USA) capable of delivering about 10 T with a rise time of 1 ms. Two ignitrons, I1 and I2 (NL7703, National Electronics, USA) were used: I1 was used to initiate discharge through the coil and I2 was used to shortcut the coil and stop the discharge through the coil (FIG. 7). In this way, the initiation of a pulse can be controlled with I1 and the termination of a pulse can be controlled by I2.

In one embodiment, capacitors that are used in stimulators of the invention can be commercially available capacitors such as the General Atomics capacitors described in http://www.ga-esi.com/EP/capacitors/series-cmf-self-healing-capacitors.php.

In the claims articles such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for neuron excitation, wherein said neuron excitation comprises dendrite excitation, said method comprising:
providing a device for dendrite excitation, said device comprising a capacitor connected to a coil and to a power supply, wherein the capacitance of said capacitor is at least 1.0 milliFarad;
subjecting a neuron to an electric field pulse longer than 250 µs in duration, induced by said device, wherein the strength of said electric field is at least 100V/m, thereby exciting said neuron.

2. The method of claim 1, wherein, said electric field pulse is equal to or longer than 1 ms in duration.

3. The method of claim 1, further comprising collecting or detecting an electric signal from said neuron.

4. The method of claim 3, wherein said collecting or detecting an electric signal from said neuron is done by Electroencephalography (EEG).

5. The method of claim 1, wherein said electric field is induced by a magnetic field, wherein said magnetic field is induced by passing current through a coil, wherein said coil is connected to a capacitor.

6. The method of claim 1, wherein said pulse duration exceeds the electric field duration threshold needed to excite a dendrite or a dendrite population.

7. A device for dendrite excitation, said device comprising a capacitor connected to a coil and to a power supply, wherein the capacitance of said capacitor is at least 1.0 milliFarad wherein said device generates an electric field pulse longer than 250 µs in duration wherein the strength of said electric field is at least 100V/m, thereby exciting said dendrite, and wherein said dendrite excitation causes a neuron to fire.

8. The device of claim 7, wherein said electric field pulse is equal to or longer than 1 ms in duration.

9. The device of claim 7, further comprising an electric signal detector or collector for collecting or detecting an electric signal from an excited neuron, wherein said detector or collector is an Electroencephalography (EEG) detector.

10. The device of claim 7, wherein said electric field is induced by a magnetic field, wherein said magnetic field is induced by passing current through a coil.

11. The device of claim 7, wherein said pulse duration exceeds the electric field duration threshold needed to excite a dendrite or a dendrite population.

* * * * *